United States Patent
Xiang et al.

(10) Patent No.: US 11,149,006 B2
(45) Date of Patent: Oct. 19, 2021

(54) COMPOUNDS AS NEUROKININ-1 RECEPTOR ANTAGONISTS AND USES THEREOF

(71) Applicant: XW LABORATORIES INC., Grand Cayman (KY)

(72) Inventors: Jia-Ning Xiang, Wuhan (CN); Xuesong Xu, Wuhan (CN); Yi Feng, Wuhan (CN); Xianbo Liu, Wuhan (CN); Wai-Si Eng, Maple Glen, PA (US)

(73) Assignee: XWPHARMA LTD., Grand Cayman (KY)

( * ) Notice: Subject to any disclaimer, the term of this patent is extended or adjusted under 35 U.S.C. 154(b) by 0 days.

(21) Appl. No.: 16/811,202

(22) Filed: Mar. 6, 2020

(65) Prior Publication Data

US 2020/0239416 A1 Jul. 30, 2020

Related U.S. Application Data

(63) Continuation of application No. PCT/CN2019/097380, filed on Jul. 24, 2019.

(30) Foreign Application Priority Data

Jul. 26, 2018 (WO) ................ PCT/CN2018/097241

(51) Int. Cl.
*C07D 211/56* (2006.01)
*A61P 1/08* (2006.01)
*A61K 9/00* (2006.01)
*A61K 45/06* (2006.01)

(52) U.S. Cl.
CPC .............. *C07D 211/56* (2013.01); *A61P 1/08* (2018.01); *A61K 9/0019* (2013.01); *A61K 9/0053* (2013.01); *A61K 45/06* (2013.01)

(58) Field of Classification Search
CPC .................................................. C07D 211/56
See application file for complete search history.

(56) References Cited

U.S. PATENT DOCUMENTS

| | | | |
|---|---|---|---|
| 5,686,615 | A | 11/1997 | Rosen |
| 5,721,255 | A | 2/1998 | Howard et al. |
| 6,329,394 | B1 | 12/2001 | Hagan et al. |
| 6,329,396 | B1 * | 12/2001 | Satake ................ C07D 211/56 514/329 |

FOREIGN PATENT DOCUMENTS

| | | |
|---|---|---|
| CN | 1088917 A | 7/1992 |
| CN | 1065264 A | 10/1992 |
| ES | 2087813 A1 | 7/1993 |

OTHER PUBLICATIONS

Altomonte "Synthetic chemistry and biological activity of pentafluorosulphanyl (SF5) organic molecules" Journal of Fluorine Chemistry (2012), 143, 57-93.*
Leroux "Trifluoromethyl ethers—synthesis and properties of an unusual substituent" Beilstein Journal of Organic Chemistry 2008, 4, No. 13.*
International Search Report and Written Opinion for Application No. PCT/CN2018/097241, dated Apr. 28, 2019, 11 pages.
International Search Report and Written Opinion for Application No. PCT/CN2019/097380, dated Oct. 8, 2019, 14 pages.
Ward et al., "Discovery of an Orally Bioavailable Nki Receptor Antagonists, (2S,3S)-(2-Methoxy-5-tetrazol-l-ylbenzyl)(2-phenylpiperidin-3-yl)amine (GR203040), with Potent Antimetic Activity", J. Med. Chem., Dec. 1995, vol. 38, p. 4985-4992.
Hansch et al., ""Aromatic" Substituent Constants for Structure-Activity Correlations", Journal of Medicinal Chemistry, 1973, vol. 16, No. 11, p. 1207-1216.
Wifp et al., "Synthesis and biological evaluation of the first pentafluorosulfanyl analogs of mefloquine", Organic Biomolecular Chemistry, Oct. 2009, vol. 7, No. 20, p. 4163-4165.
Agoni et al., "CF3-Pyridinyl Substitution on Antimalarial Therapeutics: Probing Differential Ligand Binding and Dynamical Inhibitory Effects of a Novel Triazolopyrimidine-Based Inhibitor on Plasmodium falciparum Dihydroorotate Dehydrogenase", Chemistry & Biodiversity, 2019, vol. 16, e1900365, 13 pages.
Pan et al., "Discovery of NVP-LDE225, a Potent and Selective Smoothened Antagonist", ACS Medicinal Chemistry Letters, Mar. 2010, vol. 1, pp. 130-134.
Phillips et al., "Triazolopyrimidine-based dihydroorotate dehydrogenase inhibitors with potent and selective activity against the malaria parasite, Plasmodium falciparum", NIH Journal of Medical Chemistry, Jun. 2008, vol. 51, No. 12, pp. 3649-3653.
Savoie et al., "Preparation and Utility of Organic Pentafluorosulfanyl-Containing Compounds", Chemical Reviews, American Chemical Society, 2015, vol. 115, No. 2, pp. 1130-1190.
Schneckener et al., "Prediction of Oral Bioavailability in Rats: Transferring Insights from in Vitro Correlations to (Deep) Machine Learning Models Using in Silico Model Outputs and Chemical Structure Parameters", Journal of Chemical Information and Modeling, American Chemical Society, 2019, vol. 59, No. 11, pp. 4893-4905.

(Continued)

*Primary Examiner* — David K O'Dell

(57) ABSTRACT

The present invention relates compounds of Formula (A) as NK-1 receptor antagonists, as well as their preparation and uses, and further relates pharmaceutical compositions comprising these compounds and their uses as modulators of dysfunctional glutamate transmission. The present invention also relates to the uses of the compounds or pharmaceutical compositions in treating or preventing certain disorders and diseases which relate to NK-1 receptor in humans. More specifically, the compounds and/or pharmaceutical compositions of the present invention are believed to potentially offer therapeutic benefits to patients who suffer, among others, chemotherapy-induced nausea and vomit (CINV) and/or post-operative nausea and vomit (PONV).

17 Claims, 6 Drawing Sheets

(56) References Cited

OTHER PUBLICATIONS

Sowaileh et al., "Application of the Pentafluorosulfanyl Group as a Bioisosteric Replacement", ChemMedChem, Chemistry Enabling Drug Discovery, Sep. 2017, vol. 12, No. 18, pp. 1481-1490.
Wei et al., "Identification of orally-bioavailable antagonists of the TRPV4 ion-channel", Bioorganic & Medicinal Chemistry Letters, 2015, vol. 25, pp. 4011-4015.
Welch et al., "The synthesis and biological activity of pentafluorosulfanyl analogs of fluoxetine, fenfluramine, and nonfenfluramine", Bioorganic & Medicinal Chemistry, 2007, vol. 15, pp. 6659-6666.

* cited by examiner

COMPOUNDS AS NEUROKININ-1 RECEPTOR ANTAGONISTS AND USES THEREOF

This application claims the benefit under 35 U.S.C. § 111(a) of PCT International Application No. PCT/CN2019/097380 filed on Jul. 24, 2019, which claims priority to PCT International Application No. PCT/CN2018/097241 filed on Jul. 26, 2018, each of which is incorporated by reference in its entirety.

FIELD OF THE INVENTION

The present invention relates to the field of medicinal technology, in particular, to certain compounds, their preparation and uses, as well as pharmaceutical compositions comprising such compounds. As exemplified, the present invention relates to certain compounds, their preparation, and the corresponding pharmaceutical compositions that can be potentially used in the manufacture of a medicament for preventing, treating, ameliorating certain disorder or a disease in a patient, which includes, inter alia, cancer chemotherapy-induced emesis and pruritus. It is believed that the compounds and/or pharmaceutical compositions of the present invention exert their therapeutic benefits by, among other things, acting to modulate (e.g., antagonizing) Substance P (SP) and neurokinin-1 (NK-1) receptors. More specifically, the compounds and/or pharmaceutical compositions of the present invention are believed to potentially offer therapeutic benefits to patients who suffer, among others, chemotherapy-induced nausea and vomit (CINV) and/or post-operative nausea and vomit (PONV).

BACKGROUND OF THE INVENTION

Perturbing the homeostatic binding between Substance P and NK-1 receptors (NK1R and its altered iso-forms ubiquitously distributed in neural and peripheral tissues) can lead to cascading myriads of diseases, e.g., depression, neural degeneration, alcohol addiction, pain, migraine, inflammatory bowel disease, pruritus, viral infection, bacterial infection, cancer, and emesis.

NK1R antagonists (NK1RA) have shown some emerging efficacy to treat some of these diseases: Emesis—US FDA has approved sales of 3 members of the 'pitant' class of NK1RAs aprepitant, rolapitant and netupitant to treat chemotherapy induced nausea and vomiting (CINV). NK-1 receptor antagonists also have demonstrated efficacy in clinical studies in controlling postoperative nausea and vomit (PONV) (e.g., Gan T J, et. al., *Anesth Analg.*, 112, 804-812, 2011; Apfel C C, et. al., *Curr Opin Anaesthesiol.*, 21, 427-432, 2008).

Pruritus—serlopitant showed efficacy to treat chronic/refractory pruritus in a Phase 2 trial.

Depression—despite encouraging Phase 2 clinical trial results, NK1RA's efficacy in Phase 3 trials was not statistically sustained (p<0.05) vs. comparative placebo-controlled enrollees for a variety of reasons (e.g., N. M. J. Rupniak, et. al., *J. Affect. Dis.*, 223, 121-125, 2017). Unfortunately for major depression, significant patient populations (~10-55% depending on the database accessed) are/become 'treatment resistant' to currently approved SSRI/SNRI drugs.

Cancer— despite encouraging preclinical results, some efficacy has resulted from a small clinical trial of NK1RAs. For example, NK1RAs in pre-clinical testing have efficacy to treat glioblastoma—the most common malignant brain tumor which has over-expressed NK1Rs in humans. Unfortunately, human glioblastoma while rare has a poor prognosis (mean 5-year survival rate is ~5% after initial diagnosis).

The compounds and pharmaceutical formulations disclosed in the present application are believed to exert their therapeutic benefits by, among other things, acting to modulate (e.g., antagonizing) Substance P and NK-1 receptors. As a result, the compounds and/or pharmaceutical compositions of the present invention are believed to potentially offer therapeutic benefits to patients who suffer, among others, chemotherapy-induced nausea and vomit (CINV) and/or post-operative nausea and vomit (PONV).

SUMMARY OF THE INVENTION

The following is only an overview of some aspects of the present invention but is not limited thereto. All references of this specification are incorporated herein by reference in their entirety. When the disclosure of this specification is different with citations, the disclosure of this specification shall prevail. The present invention provides compounds and pharmaceutical compositions, which modulate (e.g., antagonizing) Substance P and NK-1 receptors, their preparation, and the corresponding pharmaceutical compositions. The compounds and/or pharmaceutical compositions of the present invention can be potentially used in the manufacture of a medicament for preventing, treating, ameliorating certain disorder or a disease related to NK-1 receptor in a patient, which includes, inter alia, chemotherapy-induced nausea and vomit (CINV) and/or post-operative nausea and vomit (PONV).

One aspect of the present invention is the provision of a compound of Formula (A):

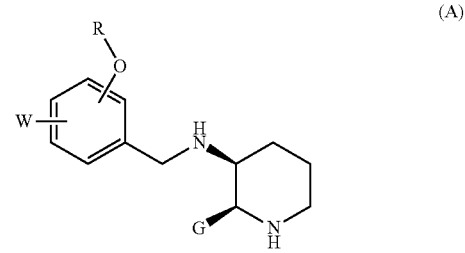

(A)

or pharmaceutically acceptable salt thereof, wherein R is H or $C_1$-$C_6$ alkyl; W is selected from the group consisting of $SF_5$, $SCF_3$, $S(O)CF_3$, and $S(O)_2CF_3$; and G is substituted or unsubstituted phenyl or a 5- or 6-membered heteroaryl.

Another aspect of the present invention is the provision of a compound of Formula (B):

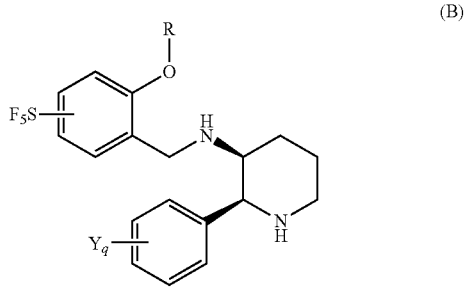

(B)

or pharmaceutically acceptable salt thereof, wherein R is H or $C_1$-$C_6$ alkyl; $Y_q$ is selected from H, halogen, $C_1$-$C_6$ alkoxy or $C_1$-$C_6$ alkyl, and q is an integer from 1 to 5, provided that when q is 2, 3, 4 or 5, $Y_1$ and $Y_2$, or $Y_3$, or $Y_4$ or $Y_5$ can be the same, or different.

In a further aspect, the invention relates to pharmaceutical compositions each comprising an effective amount of at least one compound of Formula (A) or Formula (B) or a pharmaceutically acceptable salt of a compound of Formula (A) or (B). Pharmaceutical compositions according to the invention may further comprise at least one pharmaceutically acceptable excipient, carrier, adjuvant, solvent, support or a combination thereof.

In another aspect, the invention is directed to a method of treating a subject suffering from, inter alia, certain disorder or a disease related to NK-1 receptor in a patient, which includes, inter alia, cancer chemotherapy-induced emesis and pruritus, comprising administering to the subject in need of such treatment an effective amount of at least one compound of Formula (A) or (B) or a pharmaceutically acceptable salt of a compound of Formula (A) or (B), or comprising administering to the subject in need of such treatment an effective amount of a pharmaceutical composition comprising an effective amount of at least one compound of Formula (A) or (B) or a pharmaceutically acceptable salt of a compound of Formula (A) or (B).

An aspect of the present invention concerns the use of compound of Formula (A) or (B) for the preparation of a medicament used in the treatment, prevention, inhibition or elimination of certain disorder or a disease related to NK-1 receptor in a patient, that includes, inter alia, cancer chemotherapy-induced emesis and pruritus, which medicament further comprises therapeutically effective amounts of one or more, optional, adjunctive active ingredients, which adjunctive active ingredient comprises 5-$HT_3$ antagonist (e.g., ondansetron and granisetron) and/or glucocorticoid (e.g., dexamethasone) or a combination thereof.

Another aspect of the present invention concerns the use of a compound of Formula (A) or (B) for the preparation of a medicament used in the treatment, prevention, inhibition or elimination of a disorder or disease or medical condition in a patient by modulating (e.g., antagonizing) Substance P and NK-1 receptors in a patient, which disorder or disease or medical condition includes, inter alia, chemotherapy-induced nausea and vomit (CINV) and/or post-operative nausea and vomit (PONV) in said patient.

In yet another aspect of the present invention, the compounds of Formula (A) or (B) and pharmaceutically acceptable salts thereof are useful as modulators of glutamate transmission. Thus, the invention is directed to a method for modulating glutamate transmission in a subject, comprising exposing the subject to an effective amount of at least one compound of Formula (A) or (B) or a pharmaceutically acceptable salt of a compound of Formula (A) or (B).

In yet another aspect, the present invention is directed to methods of making compounds of Formula (A) or (B) and pharmaceutically acceptable salts thereof.

In certain embodiments of the compounds, pharmaceutical compositions, and methods of the invention, the compound of Formula (A) or (B) is a compound selected from those species described or exemplified in the detailed description below or is a pharmaceutically acceptable salt of such a compound.

Another preferred embodiment, the present invention is directed to methods of preparing pharmaceutical compositions each comprising an effective amount of at least one compound of Formula (A) or (B) or a pharmaceutically acceptable salt of a compound of Formula (A) or (B). Pharmaceutical compositions according to the invention may further comprise at least one pharmaceutically acceptable excipient, carrier, adjuvant, solvent, support or a combination thereof.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (*J. Cell Sci.*, (1995) 108, 2897). The compounds of the invention may also be administered sequentially with known anticancer or cytotoxic agents when a combination formulation is inappropriate. In any combination treatment, the invention is not limited in the sequence of administration; compounds of Formula (A) or (B) may be administered either prior to or after administration of the known anticancer or cytotoxic agent. For example, the cytotoxic activity of the cyclin-dependent kinase inhibitor flavopiridol is affected by the sequence of administration with anticancer agents (*Cancer Research*, (1997) 57, 3375). Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, beads, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, $18^{th}$ Edition, (1990), Mack Publishing Co., Easton, Pa.

Liquid form preparations include solutions, suspensions and emulsions. For example, there are water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 300 mg, still more preferably from about 1 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 10 mg/day to 200 mg/day, in one to two divided doses.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and additional embodiments, features, and advantages of the invention will be apparent from the following detailed description and through practice of the invention.

BRIEF DESCRIPTION OF THE DRAWINGS

These and other aspects and advantages of embodiments of the present disclosure will become apparent and more readily appreciated from the following descriptions made with reference the accompanying schemes and drawings, in which:

FIGS. 4A-4C show the effect of Compound I and aprepitant on the total numbers of episodes, retches and vomits induced by cisplatin in a 72 h observation time.

DETAILED DESCRIPTION

Figure 1A:
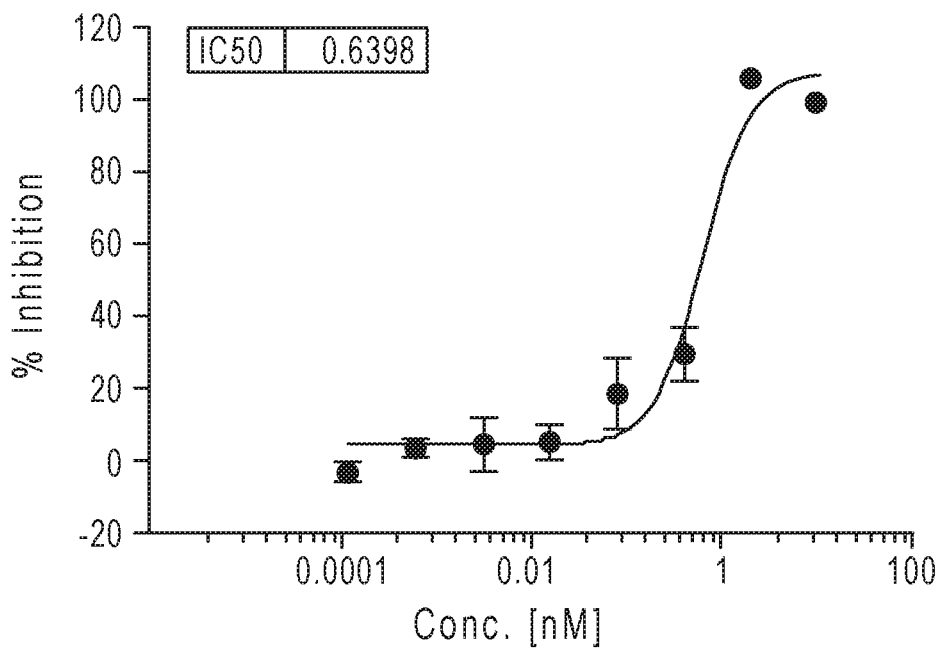
FIGS. 1A and 1B show NK-1 receptor binding affinity of Compound I.

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as are commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing", and "comprising" are used in their open, non-limiting sense.

As used herein, the singular forms "a", "an", and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

As used herein, "alkyl" refers to a saturated, straight- or branched-chain hydrocarbon group having from 1 to 12 carbon atoms. Representative alkyl groups include, but are not limited to, methyl, ethyl, n-propyl, isopropyl, 2-methyl-1-propyl, 2-methyl-2-propyl, 3-methyl-1-butyl, methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylamino" as used herein denotes an amino group as defined herein wherein one hydrogen atom of the amino group is replaced by an alkyl group as defined herein. Aminoalkyl groups can be defined by the following general formula —NH-alkyl. This general formula includes groups of the following general formulae: —NH—$C_1$-$C_{10}$ alkyl and —NH—$C_1$-$C_6$ alkyl. Examples of aminoalkyl groups include, but are not limited to aminomethyl, aminoethyl, aminopropyl, aminobutyl.

The term "dialkylamino" as used herein denotes an amino group as defined herein wherein two hydrogen atoms of the amino group are replaced by alkyl groups as defined herein. Diaminoalkyl groups can be defined by the following general formula —N(alkyl)$_2$, wherein the alkyl groups can be the same or can be different and can be selected from alkyls as defined herein, for example $C_1$-$C_{10}$ alkyl or $C_1$-$C_6$ alkyl.

The term "alkoxy" as used herein includes —O-(alkyl), wherein alkyl is defined above.

As used herein, "alkoxyalkyl" means -(alkylenyl)-O-(alkyl), wherein each "alkyl" is independently an alkyl group defined above.

The term "amino" as used herein refers to an —NH$_2$ group.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

"Aryloxy" as used herein refers to an —O-(aryl) group, wherein aryl is defined as above.

"Arylalkyl" as used herein refers to an -(alkylenyl)-(aryl) group, wherein alkylenyl and aryl are as defined above. Non-limiting examples of arylalkyls comprise a lower alkyl group. Non-limiting examples of suitable arylalkyl groups include benzyl, 2-phenethyl, and naphthalenylmethyl.

"Arylalkoxy" as used herein refers to an —O-(alkylenyl)-aryl group wherein alkylenyl and aryl are as defined above.

The term "cyano" as used herein means a substituent having a carbon atom joined to a nitrogen atom by a triple bond.

The term "cyanoalkyl" denotes an alkyl group as defined above wherein a hydrogen atom of the alkyl group is replaced by a cyano (—CN) group. The alkyl portion of the cyanoalkyl group provides the connection point to the remainder of the molecule.

The term "deuterium" as used herein means a stable isotope of hydrogen having one proton and one neutron.

The term "halogen" as used herein refers to fluorine, chlorine, bromine, or iodine. The term "halo" represents chloro, fluoro, bromo, or iodo.

The term "haloalkyl" denotes an alkyl group as defined above wherein one or more, for example one, two, or three of the hydrogen atoms of the alkyl group are replaced by a halogen atom, for example fluoro, bromo, or chloro, in particular fluoro. Examples of haloalkyl include, but are not limited to, monofluoro-, difluoro-, or trifluoro-methyl, -ethyl or -propyl, for example, 3,3,3-trifluoropropyl, 2-fluoroethyl, 2,2,2-trifluoroethyl, fluoromethyl, difluoromethyl, or trifluoromethyl, or bromoethyl or chloroethyl. Similarly, the term "fluoroalkyl" refers to an alkyl group as defined above substituted with one or more, for example one, two, or three fluorine atoms.

The term "haloalkoxy" as used herein refers to an —O-(haloalkyl) group wherein haloalkyl is defined as above. Exemplary haloalkoxy groups are bromoethoxy, chloroethoxy, trifluoromethoxy and 2,2,2-trifluoroethoxy.

The term "halosulfanyl" as used herein refers to a sulfur group having one or more halogen substituents. Example halosulfanyl groups include pentahalosulfanyl groups such as $SF_5$.

The term "hydroxy" means an —OH group.

The term "hydroxyalkyl" denotes an alkyl group that is substituted by at least one hydroxy group, for example, one, two or three hydroxy group(s). The alkyl portion of the hydroxyalkyl group provides the connection point to the remainder of a molecule. Examples of hydroxyalkyl groups include, but are not limited to, hydroxymethyl, hydroxyethyl, 1-hydroxypropyl, 2-hydroxyisopropyl, 1,4-dihydroxybutyl, and the like.

The term "oxo" means an =O group and may be attached to a carbon atom or a sulfur atom. The term "N-oxide" refers to the oxidized form of a nitrogen atom.

The term "cycloalkoxy" refers to a —O-(cycloalkyl) group.

As used herein, the term "heteroaryl" refers to a monocyclic, or fused polycyclic, aromatic heterocycle having from three to 15 ring atoms that are selected from carbon, oxygen, nitrogen, selenium and sulfur. Suitable heteroaryl groups do not include ring systems that must be charged to be aromatic, such as pyrylium. Some suitable 5-membered heteroaryl rings (as a monocyclic heteroaryl or as part of a polycyclic heteroaryl) have one oxygen, sulfur, or nitrogen atom, or one nitrogen plus one oxygen or sulfur, or 2, 3, or 4 nitrogen atoms. Some suitable 6-membered heteroaryl rings (as a monocyclic heteroaryl or as part of a polycyclic heteroaryl) have 1, 2, or 3 nitrogen atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Those skilled in the art will recognize that the species of heteroaryl, and cycloalkyl groups listed or illustrated above are not exhaustive, and that additional species within the scope of these defined terms may also be selected.

As described herein, compounds disclosed herein may optionally be substituted with one or more substituents, or as exemplified by particular classes, subclasses, and species of the invention.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl, alkylenyl, heteroaryl, $R_1$, $R_2$, or $R_a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4, while a range expressed as "10-20%" includes 10%, 11%, 12%, 13%, 14%, 15%, 16%, 17%, 18%, 19% and 20%. Similarly, numerical ranges are also intended to include sequential fractional integers. For example, a range expressed as "1-2%" would include 1.0%, 1.1%, 1.2%, 1.3%, 1.4%, 1.5%, 1.6%, 1.7%, 1.8%, 1.9% and 2.0%.

When a multifunctional moiety is shown, the point of attachment to the core is indicated by a line or hyphen. For example, aryloxy—refers to a moiety in which an oxygen atom is the point of attachment to the core molecule while aryl is attached to the oxygen atom.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given protein, receptor and/or ion channels.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein, the terms "administration of" and "administering a" compound should be understood to mean providing a compound of the invention, pharmaceutical composition comprising a compound or a prodrug of a compound of the invention to an individual in need thereof. It is recognized that one skilled in the non-limiting art can treat a patient presently afflicted with neurological and psychiatric disorders or by prophylactically treat a patient afflicted with the disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the other types of reactions or interactions such as to cause the dissociation of one or more of the ingredients. Accordingly, the pharmaceutical compositions of the present invention encompass any composition made by mixing a compound of the present invention and a pharmaceutically acceptable carrier.

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

"Stereoisomer" refers to compounds which have identical chemical constitution but differ with regard to the arrangement of the atoms or groups in space. Stereoisomers include enantiomer, diastereomers, conformer (rotamer), geometric (cis/trans) isomer, atropisomer etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents or resolved using conventional techniques. If the compound contains a double bond, the substituent may be E or Z configuration. If the compound contains a disubstituted cycloalkyl, a cycloalkyl substituent may have a cis- or trans-configuration relative to another substituent of the same cycloalkyl frame.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aube, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column.

The compounds of the invention can form pharmaceutically acceptable salts, which are also within the scope of this invention. A "pharmaceutically acceptable salt" refers to a salt of a free acid or base of a compound of Formula I that is non-toxic, is physiologically tolerable, is compatible with the pharmaceutical composition in which it is formulated and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxyic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, *Journal of Pharmaceutical Sciences* (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., *J. Pharmaceutical Sci.*, 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al, *AAPS PharmSciTech.*, 5(1), article 12 (2004); and A. L. Bingham et al, *Chem. Commun.*, 603-604 (2001). A typical, non-limiting process involves dissolving the compound of the invention in a suitable amount of the solvent (organic solvent or water or a mixture thereof) at a higher than ambient temperature and cooling the solution at a rate sufficient to form crystals which are then isolated by standard methods. Analytical techniques such as, for example, infrared spectroscopy, show the presence of the solvent (or water) in the crystals as a solvate (or hydrate).

The present invention also relates to pharmaceutically active metabolites of compounds of Formula (A) or (B) and uses of such metabolites in the methods of the invention. A "pharmaceutically active metabolite" means a pharmacologically active product of metabolism in the body of a compound of Formula (A) or (B) or salt thereof. Active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^{2}H$ or $^{3}H$), detection or imaging techniques [such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," and the like, with respect to the compounds described herein is intended to apply equally to the salt, solvate, and polymorph forms of enantiomers, stereoisomers, rotamers, tautomers, atropisomers, and racemates of the compounds of the invention.

The present invention relates to particular molecules and pharmaceutically acceptable salts or isomers thereof. The invention further relates to molecules which are useful in modulating neurokinin-1 (NK-1) receptor and pharmaceutically acceptable salts, solvates, esters, or isomers thereof.

The compounds provided by the present disclosure exhibit an oral bioavailability (F %) in rats, for example, greater than 10%, greater than 15%, greater than 20% or greater than 25%.

The compounds provided by the present disclosure are NK-1 antagonists and exhibit a inhibitory potency (IC50) to the NK-1 receptor of less than 1 nM.

The invention is directed to compounds as described herein and pharmaceutically acceptable salts, solvates, esters, or isomers thereof, and pharmaceutical compositions comprising one or more compounds as described herein and pharmaceutically acceptable salts or isomers thereof. One aspect of this invention is the provision of compounds, compositions, kits, and antidotes for modulating NK-1 receptor in mammals having a compound of the Formula (A):

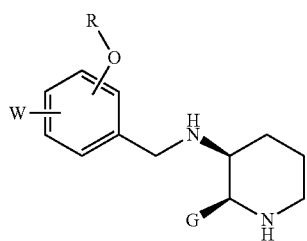

(A)

or pharmaceutically acceptable salt thereof, wherein R is H or $C_1$-$C_6$ alkyl; W is selected from the group consisting of $SF_5$, $SCF_3$, $S(O)CF_3$, and $S(O)_2CF_3$; G is substituted or unsubstituted phenyl or a 5- or 6-membered heteroaryl.

Another aspect of this invention is the provision of compounds, compositions, kits, and antidotes for modulating NK-1 receptor in mammals having a compound of the Formula (B):

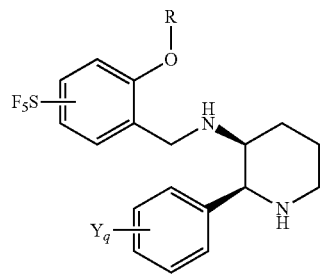

(B)

or pharmaceutically acceptable salt thereof, wherein R is H or $C_1$-$C_6$ alkyl; $Y_q$ is selected from H, halogen, $C_1$-$C_6$ alkoxy or $C_1$-$C_6$ alkyl, and q is an integer from 1 to 5, provided that when q is 2, 3, 4 or 5, $Y_1$ and $Y_2$, or $Y_3$, or $Y_4$ or $Y_5$ can be the same, or different.

In some embodiments, for compounds having the general Formula (B), R is preferably selected from the group consisting of H and $C_1$-$C_3$ alkyl. In yet other embodiments, in which for compounds having the general Formula (B), R is H, methyl, ethyl or isopropyl.

In yet other embodiments, for compounds having the general Formula (B), $Y_q$ is preferably selected from the group consisting of H, fluorine, chlorine, $C_1$-$C_3$ alkyl and $C_1$-$C_3$ alkoxy, and q is preferably 1. In still other embodiments, in which for compounds having the general Formula (B), Y is H, methyl, ethyl, isopropyl, methoxy, ethoxy or isopropoxy.

An embodiment of the invention is the provision of a compound, where the various moieties are independently selected, R is methyl, and Y is selected from the group consisting of H, methyl, ethyl, isopropyl, methoxy, ethoxy and isopropoxy.

Another embodiment of the invention is the provision of a compound, where the various moieties are independently selected, R is methyl, and Y is H.

Another embodiment of the invention is the provision of a compound, where the various moieties are independently selected, R is ethyl, and Y is selected from the group consisting of H, methyl, ethyl, isopropyl, methoxy, ethoxy and isopropoxy.

Another embodiment of the invention is the provision of a compound, where the various moieties are independently selected, R is isopropyl, and Y is selected from the group consisting of H, methyl, ethyl, isopropyl, methoxy, ethoxy and isopropoxy.

Another embodiment of the invention is the provision of a compound, wherein any of the carbon-hydrogen bond can be replaced with a carbon-deuterium bond.

In certain embodiments of the present invention is the provision of compounds, compositions, kits, and antidotes for modulating NK-1 receptor in mammals having a compound that is further illustrated by the following compound group consisting of:

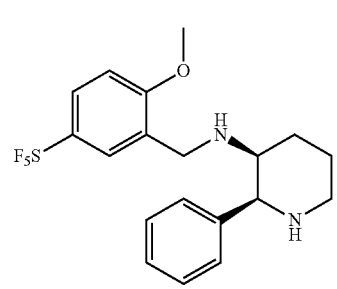

I

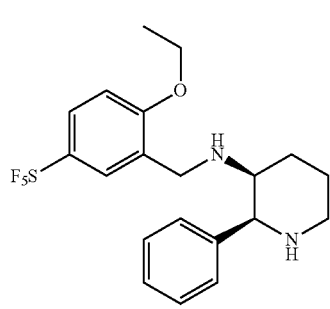

II

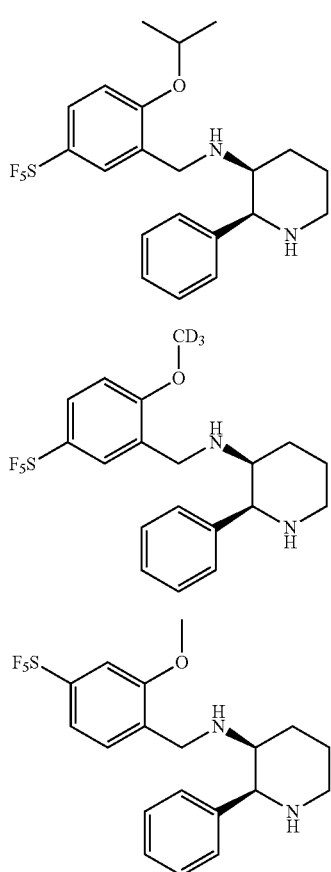

and pharmaceutically acceptable salts thereof.

In another embodiments of the present invention is the provision of a compound, which is (2S,3S)—N-(2-methoxy-5-(pentafluorosulfanyl)benzyl)-2-phenylpiperidin-3-amine and its pharmaceutically acceptable salts.

An aspect of the present invention concerns compounds disclosed herein.

An aspect of the present invention concerns compounds which are or can be modulators (antagonists) of NK-1 receptor.

An aspect of the present invention concerns the use of a modulator (antagonist) of NK-1 receptor for the preparation of a medicament used in the treatment, prevention, inhibition or elimination of tumors.

An aspect of the present invention concerns the use of a modulator (antagonist) of NK-1 receptor for the preparation of a medicament used in the treatment, prevention, inhibition or elimination of a disorder or disease or medical condition in a patient by modulating (antagonizing) NK-1 receptor in said patient, wherein said disorder or disease or medical condition is related to NK-1 receptor in a patient, which includes, inter alia, chemotherapy-induced nausea and vomit (CINV) and/or post-operative nausea and vomit (PONV).

The present invention also describes one or more methods of synthesizing the compounds of the present invention.

The invention also describes one or more uses of the compounds of the present invention.

The invention also describes one or more uses of the compounds of the present invention with an adjunctive agent such as use with 5-HT$_3$ antagonist (e.g., ondansetron and granisetron) and/or glucocorticoid (e.g., dexamethasone).

The present invention also describes one or more methods of preparing various pharmaceutical compositions comprising the compounds of the present invention.

The invention also describes one or more uses of the various pharmaceutical compositions of the present invention for the preparation of a medicament used in the treatment, prevention, inhibition or elimination of a disorder or disease or medical condition related to NK-1 receptor in a patient, which includes, inter alia, chemotherapy-induced nausea and vomit (CINV) and/or post-operative nausea and vomit (PONV) by modulating (antagonizing) NK-1 receptor in said patient.

The present invention provides a pharmaceutical composition comprising a therapeutically effective amount of at least one compound of the present invention, e.g., example compounds and its pharmaceutically acceptable salts. According to the specific examples of the present invention, the pharmaceutical composition can further comprise pharmaceutically acceptable excipient, carrier, adjuvant, solvent and a combination thereof.

In one embodiment, the pharmaceutical composition can comprise therapeutically effective amounts of one or more, optional, adjunctive active ingredients.

In another embodiment, the present invention provides a pharmaceutical composition comprising therapeutically effective amount of at least one adjunctive active compound which is for treating a physiological disorder or disease associated with NK-1 receptor activity.

The present invention further provides a method of treating, preventing or ameliorating a disease or disorder, comprising administrating a safe and effective amount of a combination of drugs containing compounds of the invention and one or more therapeutic active agents. Among them, the combination of drugs comprises one or more additional drugs for treatment of neurological and psychiatric disorders and diseases of central nervous system.

Other drugs for treatment of neurological and psychiatric disorders and diseases of central nervous system include, but are not limited to: an antipsychotic, an atypical antipsychotic, an antiepileptic, an anti-Parkinson's disease drug, an anti-amyotrophic lateral sclerosis drug, anti-pain drug or any combination thereof.

Still other drugs involved in one, or more, specific use(s) of the compounds of the present invention, such as in a combination treatment of chemotherapy-induced nausea and vomit (CINV) and/or post-operative nausea and vomit (PONV), are adjunctive agents, such as 5-HT3 antagonist (e.g., ondansetron and granisetron) and/or glucocorticoid (e.g., dexamethasone).

The amount of the compound of the pharmaceutical composition disclosed herein refers to an amount which can be effectively detected to modulate dysfunctional glutamate transmission of biology samples and in a patient. The active ingredient may be administered to subjects in need of such treatment in dosage that will provide optimal pharmaceutical efficacy, which is not limited to the desired therapeutic effects, on the route of administration, and on the duration of the treatment. The dosage will vary from patient to patient depending upon the nature and severity of disease, the patient's weight, special diet then being followed by a patient, concurrent medication, and other factors which those skilled in the art will recognize. The quantity of active compound in a unit dose of preparation may be varied or adjusted from about 1 mg to about 1000 mg, preferably from about 1 mg to about 500 mg, more preferably from about 1 mg to about 300 mg, still more preferably from about 1 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 10 mg/day to 200 mg/day, which may be administered in single or multiple doses. In yet another embodiment about 1 mg to 50 mg per patient per day.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof provide, directly or indirectly, a compound as otherwise described herein, or a therapeutically effective metabolite or residue thereof.

The pharmaceutical compositions of the invention may be prepared and packaged in bulk form wherein a safe and effective amount of a compound of Formula (A) disclosed herein can be extracted and then given to the patient, such as with powders or syrups. Generally, dosage levels of between 0.0001 to 10 mg/kg of body weight daily are administered to the patient to obtain effective modulation of dysfunctional glutamate transmission. Alternatively, the pharmaceutical compositions of the invention may be prepared and packaged in unit dosage form wherein each physically discrete unit contains a safe and effective amount of a compound of Formula (A) disclosed herein. When prepared in unit dosage form, the pharmaceutical compositions of the invention commonly contain from about 0.5 mg to 1 g, or 1 mg to 500 mg, or 5 mg to 200 mg, or more preferably, 25 mg to 100 mg of the compound of the invention.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient in the combination should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are resources that are available to the skilled artisan that describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared for example at normal ambient temperature and pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and ascorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a sterile vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (A) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research,* 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminum stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered via one or more applications per day to the affected area; over skin areas occlusive dressings may advantageously be used. Continuous or prolonged delivery may be achieved via an adhesive reservoir system.

Compounds or pharmaceutical compositions of the invention disclosed herein can be used in the manufacture of a medicament for treating, preventing, ameliorating or mitigating a disorder or disease in a subject, as well as other medicaments for modulating (e.g., antagonizing) Substance P (SP) and neurokinin-1 (NK-1) receptors, and the compounds of this invention have superior pharmacokinetic and pharmacodynamic properties, fewer toxic side-effect.

Specifically, the amount of the compound of compositions of the present invention can effectively and detectably modulate (e.g., antagonizing) Substance P (SP) and neurokinin-1 (NK-1) receptors. The compounds or pharmaceutical compositions of the invention may be used for preventing, treating or alleviating diseases relating to Substance P (SP) and neurokinin-1 (NK-1) receptors, wherein such diseases which includes, inter alia, chemotherapy-induced nausea and vomit (CINV) and/or post-operative nausea and vomit (PONV).

In one embodiment, the present invention provides a pharmaceutical composition comprising therapeutically effective amount of at least one adjunctive active compound is for treating chemotherapy-induced nausea and vomit (CINV) and/or post-operative nausea and vomit (PONV), and the adjunctive active ingredient comprises a serotonin 5-HT$_3$ antagonist, comprising ondansetron and granisetron, or glucocorticoid comprising dexamethasone.

In another embodiment, the present invention provides a use of the pharmaceutical composition in the manufacture of a medicament for treating or lessening the symptoms of a physiological disorder or disease in a patient by modulating NK-1 receptor activity in said patient.

In yet another embodiment, the present invention provides a use of the pharmaceutical composition in the manufacture of a medicament for treating or lessening the symptoms of a disorder or disease which comprises chemotherapy-induced nausea and vomit (CINV) and or post-operative nausea and vomit (PONV).

In still another embodiment, the present invention provides a use of the pharmaceutical composition in the manufacture of a medicament for use in treating or lessening the symptoms of a physiological disorder or disease in a human patient by modulating NK-1 receptor activity in said patient.

In still another embodiment, the present invention provides a use of the pharmaceutical composition in the manufacture of a medicament for use in treating or lessening the symptoms of a physiological disorder or disease in a human patient by modulating NK-1 receptor activity in said patient, wherein the disorder or disease is chemotherapy-induced nausea and vomit (CINV) and/or post-operative nausea and vomit (PONV).

In still another embodiment, the present invention further provides a method for treating or lessening the symptoms of a physiological disorder or disease in a patient by modulating NK-1 receptor activity in said patient comprising administering to the patient a therapeutically effective amount of a compound of the present invention or a pharmaceutical composition of the foregoing.

In still another embodiment, the present invention further provides a method for treating or lessening the symptoms of a physiological disorder or disease in a patient by modulating NK-1 receptor activity in said patient comprising administering to the patient a therapeutically effective amount of a compound of the present invention or a pharmaceutical composition of the foregoing, wherein the disorder or disease is chemotherapy-induced nausea and vomit (CINV) and post-operative nausea and vomit (PONV).

In still another embodiment, the present invention further provides a method for treating or lessening the symptoms of a physiological disorder or disease in a patient by modulating NK-1 receptor activity in said patient comprising administering to the patient a therapeutically effective amount of a compound of the present invention or a pharmaceutical composition of the foregoing.

In still another embodiment, the aforementioned disorder or disease is chemotherapy-induced nausea and vomit (CINV).

In still another embodiment, the present invention further provides a method of treating chemotherapy-induced nausea and vomit (CINV) in a patient in need of such treatment comprising administering to the patient an effective amount of at least one compound of the present invention or the foregoing pharmaceutical composition and in combination with an effective amount of at least one serotonin 5-$HT_3$ receptor antagonist and/or at least one glucocorticoid.

In still another embodiment, the present invention further provides a method of treating chemotherapy-induced nausea and vomit (CINV) in a patient in need of such treatment comprising administering to the patient an effective amount of at least one compound of the present invention, or the foregoing pharmaceutical composition, together with a serotonin 5-$HT_3$ receptor antagonist, which is ondansetron and/or granisetron, or a glucocorticoid, which is dexamethasone, or a pharmaceutically acceptable salt of the foregoing.

In another aspect of the present invention, as it is well known, chemotherapy-induced nausea and vomit (CINV) has a significant negative impact on the quality of life of cancer patients. Failure to adequately manage CINV often influences patient compliance with chemotherapeutic regimens and even patient decisions on whether to undergo chemotherapeutic treatment. Traditional regimens to prevent CINV generally involved a combination of a corticosteroid plus a 5-$HT_3$ receptor antagonist that is usually implemented for alleviating acute emesis reaction. In the past two decades, antiemetic treatment has greatly advanced with the availability of NK-1 receptor antagonist (e.g., aprepitant and its prodrug fosaprepitant). NK-1 receptor antagonists have a mechanism of action by blocking binding of substance P to NK-1 receptor in the brain stem emetic center distinct from corticosteroids and 5-$HT_3$ receptor antagonist, thus their use can complement traditional antiemetic drugs and can enhance control of CINV, especially those related to delayed phase CINV.

In still another aspect of the present invention, known antiemetic guidelines categorize chemotherapy according to emetogenic risk potential into four levels: highly emetogenic chemotherapy (HEC, >90%), moderately emetogenic chemotherapy (MEC, 31-90%), low emetogenic chemotherapy (10-30%), and minimally emetogenic chemotherapy (<10%). Currently, the combination of corticosteroid, 5-$HT_3$ antagonist and NK-1 receptor antagonist has been largely recommended by guidelines as standard treatment to control CINV risk in patients receiving HEC or MEC.

In one embodiment, the therapies disclosed herein comprise administrating a safe and effective amount of the compound of the invention or the pharmaceutical composition containing the compound of the invention to patients in need. Each example disclosed herein comprises the method of treating the diseases above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal and is typically by injection or infusion. Parenteral administration includes intravenous, intramuscular, and subcutaneous injection or infusion. Topical administration includes application to the skin as well as intraocular, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasal.

In one embodiment, the compound of the invention or the pharmaceutical composition thereof may be administered once or according to a dosing regimen wherein multiple doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as its absorption, distribution, and half-lives of metabolism and elimination, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's tolerance to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties can be correlated with in vitro and in vivo tests using advantageously mammals, e.g., mice, rats, dogs, non-human primates, such as monkeys or isolated organs, tissues and preparations thereof. The compounds of the present invention can be applied in vitro in the form of solutions, e.g., preferably aqueous solutions, and in vivo via topically, inhalingly, enterally or parenterally, advantageously intravenously, e.g., as a suspension or in aqueous solution.

In one embodiment, a therapeutically effective dosage of the compound disclosed herein from about 0.1 mg to about 1,000 mg per day. The pharmaceutical compositions should provide a dosage of from about 0.1 mg to about 1,000 mg of the compound. In a special embodiment, pharmaceutical dosage unit forms are prepared to provide from about 1 mg to about 1,000 mg, about 10 mg to about 500 mg, about 20 mg to about 200 mg, about 25 mg to about 100 mg, or about 30 mg to about 60 mg of the active ingredient or a combination of essential ingredients per dosage unit form. In a special embodiment, pharmaceutical dosage unit forms are prepared to provide about 1 mg, 5 mg, 10 mg, 20 mg, 25 mg, 50 mg, 100 mg, 250 mg, 500 mg, 1000 mg of the active ingredient.

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (A) above, except where further noted. The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arcos Chemical Company and Alfa Chemical Company, and were used without further purification unless otherwise indicated.

Compounds of the present invention, including salts, esters, hydrates, or solvates thereof, can be prepared using any known organic synthesis techniques and can be synthesized according to any of numerous possible synthetic routes.

The reactions for preparing compounds of the present invention can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

Compounds of the present invention can be synthesized using the methods described below, together with synthetic methods known in the art of synthetic organic chemistry, or variations thereon as appreciated by those skilled in the art. Preferred methods include but are not limited to those methods described below. Specifically, the compounds of the present invention of Formula (A-B) can be synthesized by following the steps outlined in the exemplary general synthetic schemes listed below, and the abbreviations for the reactants or for the chemical groups of the reactants included in the synthetic schemes are defined in the Examples.

General synthetic schemes (1-2) towards compounds having Formula (B) are shown as follows:

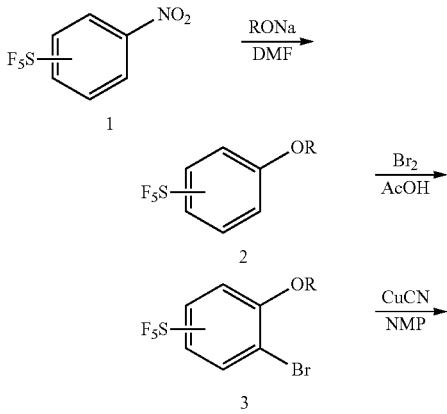

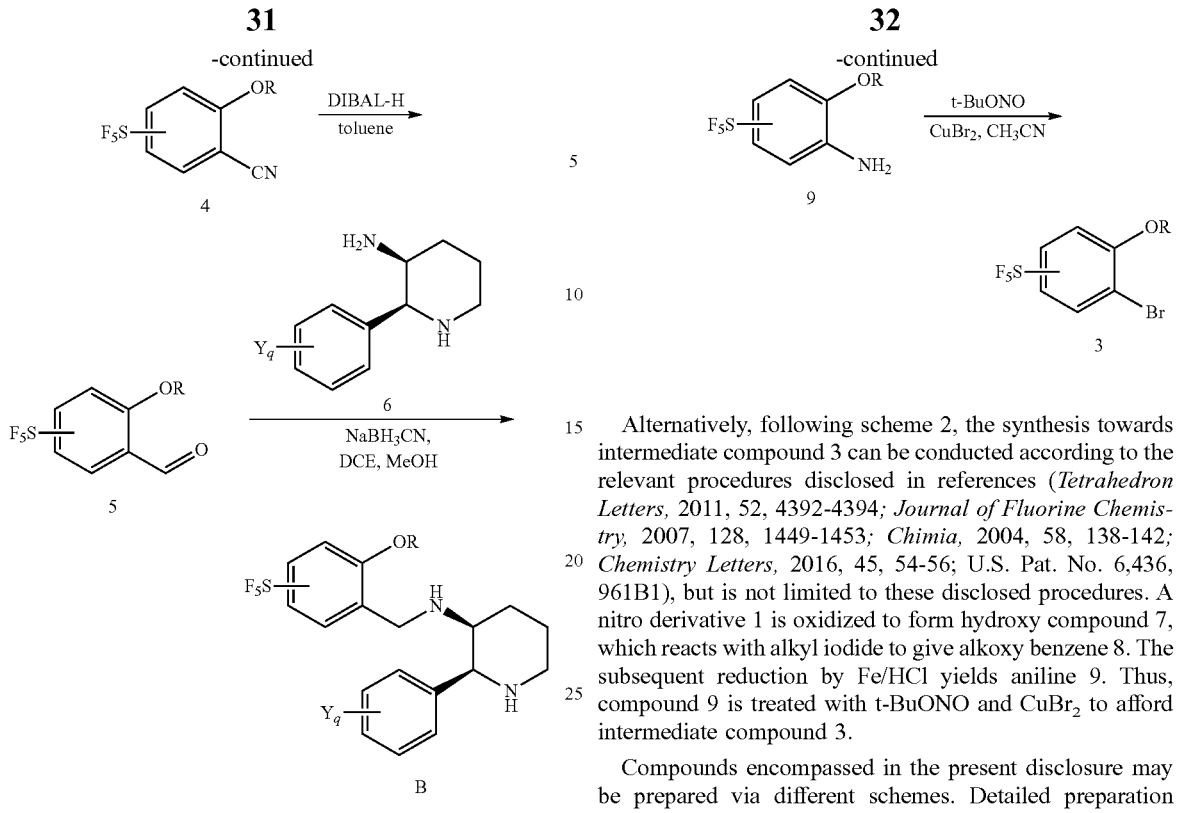

Following scheme 1, the synthesis towards compounds having Formula (B) can be conducted according to the relevant procedures disclosed in references (*Journal of Organic Chemistry*, 2014, 79, 18, 8906-8911; *Organic Letters*, 2011, 13, 6, 1466-1469; *Journal of Medicinal Chemistry*, 2017, 60, 4135-4146; *Chimia*, 2004, 58, 138-142; *Chemistry Letters*, 2016, 45, 54-56; U.S. Pat. No. 6,436, 961B1; WO2012045290A1), but is not limited to these disclosed procedures. A nitro derivative 1 is treated with sodium alkoxide to form alkoxy benzene derivative 2. The subsequent bromination gives bromide 3, which is substituted and further reduced to yield benzyl aldehyde 5. Thus, the reductive amination of compound 5 with amine 6 affords substituted piperidine compound (B).

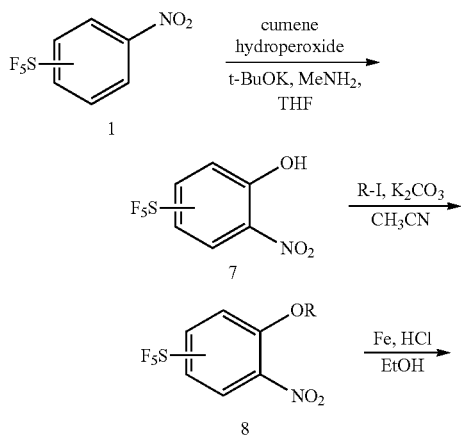

Alternatively, following scheme 2, the synthesis towards intermediate compound 3 can be conducted according to the relevant procedures disclosed in references (*Tetrahedron Letters*, 2011, 52, 4392-4394; *Journal of Fluorine Chemistry*, 2007, 128, 1449-1453; *Chimia*, 2004, 58, 138-142; *Chemistry Letters*, 2016, 45, 54-56; U.S. Pat. No. 6,436, 961B1), but is not limited to these disclosed procedures. A nitro derivative 1 is oxidized to form hydroxy compound 7, which reacts with alkyl iodide to give alkoxy benzene 8. The subsequent reduction by Fe/HCl yields aniline 9. Thus, compound 9 is treated with t-BuONO and CuBr$_2$ to afford intermediate compound 3.

Compounds encompassed in the present disclosure may be prepared via different schemes. Detailed preparation processes of 5 exemplary compounds via various schemes are described below and the characterization results are listed as well.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodecamolybdophosphoric acid in ethanol and subsequent heating. Column chromatography was performed using silica gel (200-400 mesh) from commercial suppliers. $^1$H NMR spectra were recorded on an Agilent 400-MR NMR spectrometer (400.00 MHz for 1 H) at room temperature. Solvent signal was used as reference for $^1$H NMR (CDCl$_3$, 7.26 ppm; CD$_3$OD, 3.31 ppm; DMSO-d6, 2.50 ppm; D$_2$O, 4.79 ppm). The following abbreviations were used to explain the multiplicities: s=singlet, d=doublet, t=triplet, q=quartet, br. s.=broad singlet, dd=double doublet, td=triple doublet, dt=double triplet, dq=double quartet, m=multiplet. Other abbreviations used in the experimental details are as follows: δ=chemical shift in parts per million downfield from tetramethylsilane, Ar=aryl, Ac=acyl, Boc=tert-butyloxy carbonyl, Bn=Benzyl, DCM=dichloromethane, DCE=dichloroethane, DMF=N,N'-dimethylformamide, NMP=N-methyl-2-pyrrolidone, DIBAL-H=diisobutyl aluminium hydride, DIPEA=diisopropylethylamine, DMAP=4-(dimethylamino) pyridine, DMSO=dimethyl sulphoxide, EA=ethyl acetate, Et=ethyl, Me=methyl, Hz=hertz, HPLC=high performance liquid chromatography, J=coupling constant (in NMR), min=minute(s), h=hour(s), NMR=nuclear magnetic resonance, prep=preparative, PE=petroleum ether, t-Bu=tert-butyl, iPr=isopropyl, TBAF=tetrabutylammonium fluoride, tert=tertiary, TFA=trifluoroacetic acid, THF=tetrahydrofuran, TLC=thin-layer chromatography.

Aspects

The invention is further defined by the following aspects.

Aspect 1. A compound having the structure of Formula (A):

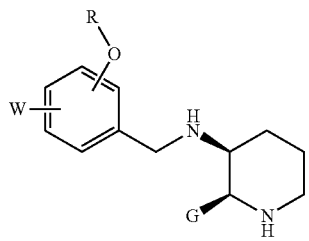

(A)

or pharmaceutically acceptable salt thereof, wherein,
R is selected from the group consisting of H and $C_1$-$C_6$alkyl;
W is selected from the group consisting of $SF_5$, $SCF_3$, $S(O)CF_3$, and $S(O)_2CF_3$; and
G is selected from the group consisting of substituted phenyl, unsubstituted phenyl, and $C_5$-$C_6$ heteroaryl.

Aspect 2. The compound according to aspect 1, wherein R is hydrogen.

Aspect 3. The compound according to aspect 1, wherein R is $C_{1-3}$ alkyl.

Aspect 4. The compound according to any one of aspects 1 to 3, wherein W is $SF_5$.

Aspect 5. The compound according to any one of aspects 1 to 4, wherein G is substituted phenyl.

Aspect 6. The compound according to any one of aspects 1 to 4, wherein G is phenyl.

Aspect 7. The compound according to any one of aspects 1 to 4, wherein G is $C_5$-$C_6$ heteroaryl.

Aspect 8. The compound according to any one of aspects 1 to 5, wherein any of the carbon-hydrogen bond can be replaced with a carbon-deuterium bond.

Aspect 9. The compound according to aspect 1, wherein, R is selected from the group consisting of methyl, ethyl, and isopropyl; W is $SF_5$; and G is phenyl.

Aspect 10. The compound according to aspect 1, wherein, R is selected from the group consisting of methyl, ethyl, and isopropyl; W is $SF_5$, wherein W is substituted at the 5-position of the phenyl ring; and G is phenyl.

Aspect 11. The compound according to aspect 1, wherein, R is methyl; W is $SF_5$; and G is phenyl.

Aspect 12. The compound according to aspect 1, wherein, R is methyl; W is $SF_5$, wherein W is substituted at the 5-position of the phenyl ring; and G is phenyl.

Aspect 13. The compound according to aspect 1, wherein the compound has the structure of Formula (B):

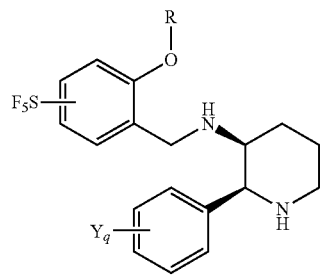

(B)

or pharmaceutically acceptable salt thereof, wherein, R is selected from the group consisting of H and $C_1$-$C_6$alkyl; $Y_q$ is selected from the group consisting of H, halogen, $C_1$-$C_6$ alkoxy and $C_1$-$C_6$ alkyl; and q is an integer from 1 to 5, provided that when q is 2, 3, 4 or 5, $Y_1$ and $Y_2$, or $Y_3$, or $Y_4$ or $Y_5$ can be the same, or different.

Aspect 14. The compound according to aspect 13, wherein R is selected from the group consisting of H and $C_1$-$C_3$ alkyl.

Aspect 15. The compound according to aspect 13, wherein, $Y_q$ is selected from the group consisting of H, fluorine, chlorine, $C_1$-$C_3$ alkyl and $C_1$-$C_3$ alkoxy; and q is 1.

Aspect 16. The compound according to aspect 13, wherein R is selected from the group consisting of H, methyl, ethyl, and isopropyl.

Aspect 17. The compound according to aspect 13, wherein, $Y_q$ is selected from the group consisting of H, methyl, ethyl, isopropyl, methoxy, ethoxy, and isopropoxy; and q is 1.

Aspect 18. The compound according to claim 13, wherein, R is methyl; $Y_q$ is selected from the group consisting of H, methyl, ethyl, isopropyl, methoxy, ethoxy, and isopropyl; and q is 1.

Aspect 19. The compound according to aspect 13, wherein, R is ethyl; and $Y_q$ is selected from the group consisting of H, methyl, ethyl, isopropyl, methoxy, ethoxy and isopropoxy.

Aspect 20. The compound according to aspect 13, wherein, R is isopropyl; and $Y_q$ is selected from the group consisting of H, methyl, ethyl, isopropyl, methoxy, ethoxy and isopropoxy.

Aspect 21. The compound according to aspect 1, wherein the compound is selected from the group consisting of Compound (I), Compound (II), Compound (III), Compound (IV), and Compound (V):

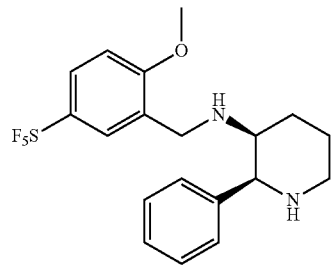

I

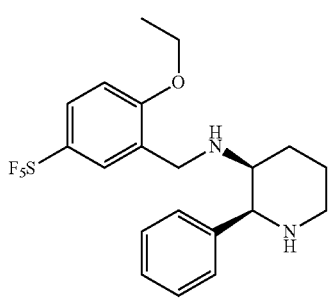

II

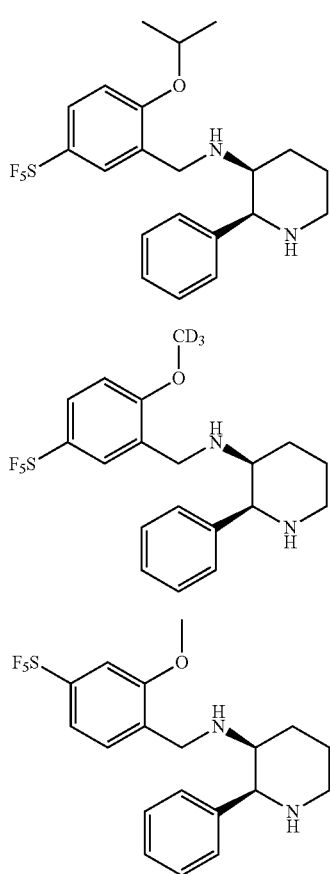

or pharmaceutically acceptable salt of any of the foregoing.

Aspect 22. The compound according to aspect 1, wherein the compound is (2S,3S)—N-(2-methoxy-5-(pentafluorosulfanyl)benzyl)-2-phenylpiperidin-3-amine or a pharmaceutically acceptable salt thereof.

Aspect 23. A pharmaceutical composition comprising a therapeutically effective amount of at least one compound according to any one of aspects 1 to 22, or a pharmaceutically acceptable salt thereof.

Aspect 24. The pharmaceutical composition of aspect 23, wherein the pharmaceutical composition further comprises a pharmaceutically acceptable excipient, carrier, adjuvant, solvent, support, or a combination of any of the foregoing.

Aspect 25. The pharmaceutical composition according to aspect 24, wherein the pharmaceutical composition further comprises a therapeutically effective amounts of one or more, optional, adjunctive active ingredients.

Aspect 26. The pharmaceutical composition according to aspect 25, wherein the adjunctive active ingredient comprises a compound effective for treating a physiological disorder or disease associated with NK-1 receptor activity.

Aspect 27. The pharmaceutical composition according to aspect 26, wherein the adjunctive active ingredient comprises a compound effective for treating chemotherapy-induced nausea and vomiting (CINV) and/or post-operative nausea and vomiting (PONV).

Aspect 28. The pharmaceutical composition according to aspect 26, wherein the adjunctive active ingredient comprises a serotonin 5-$HT_3$ antagonist, a glucocorticoid, or a combination thereof.

Aspect 29. The pharmaceutical composition according to aspect 26, wherein the adjunctive active ingredient comprises ondansetron, granisetron, dexamethasone, or a combination of any of the foregoing.

Aspect 30. The pharmaceutical composition according to any one of aspects 23 to 29, wherein the pharmaceutical composition is an oral formulation.

Aspect 31. The pharmaceutical composition according to any one of aspects 23 to 30, wherein the pharmaceutical composition is an oral dosage form.

Aspect 32. The pharmaceutical composition according to any one of aspects 23 to 29, wherein the pharmaceutical composition is an intravenous formulation.

Aspect 33. Use of the compound according to any one of aspects 1 to 22 or the pharmaceutical composition according to any one of aspects 23 to 32 in the manufacture of a medicament for treating or lessening the symptoms of a physiological disorder or disease in a patient.

Aspect 34. The use according to aspect 33, wherein the etiology of the physiological disorder or disease is associated with NK-1 receptor activity.

Aspect 35. The use of the compound or pharmaceutical composition according to aspect 33, wherein the physiological disorder or disease comprises chemotherapy-induced nausea and vomiting (CINV) or post-operative nausea and vomiting (PONV).

Aspect 36. The compound according to any one of aspects 1 to 22 or the pharmaceutical composition according to any one of aspects 23 to 32 for use in treating or lessening the symptoms of a physiological disorder or disease in a human patient by modulating NK-1 receptor activity in said patient.

Aspect 37. The compound or pharmaceutical composition for use according to aspect 36, wherein the physiological disorder or disease is chemotherapy-induced nausea and vomiting (CINV) or post-operative nausea and vomiting (PONV).

Aspect 38. A method for treating or lessening the symptoms of a physiological disorder or disease in a patient by modulating NK-1 receptor activity in said patient comprising administering to the patient a therapeutically effective amount of a compound according to any one of aspects 1 to 22 or a pharmaceutically acceptable salt thereof, or a pharmaceutical composition according to any one of aspects 23 to 32.

Aspect 39. The method according to aspect 38, wherein administering comprises orally administering.

Aspect 40. The method according to aspect 38, wherein administering comprises administering intravenously.

Aspect 41. The method according to any one of aspects 38 to 40, wherein the physiological disorder or disease is chemotherapy-induced nausea or vomiting (CINV) and post-operative nausea and vomiting (PONV).

Aspect 42. A method for treating or lessening the symptoms of a physiological disorder or disease in a patient by modulating NK-1 receptor activity in said patient comprising administering to the patient a therapeutically effective amount of a compound according to aspect 22 or a pharmaceutically acceptable salt thereof, or a pharmaceutical composition according to any one of aspects 23 to 32, wherein the compound is the compound according to aspect 22 or a pharmaceutically acceptable salt thereof.

Aspect 43. The method according to aspect 42, wherein administering comprises orally administering.

Aspect 44. The method according to aspect 42, wherein administering comprises administering intravenously.

Aspect 45. The method according to any one of aspects 42 to 44, wherein the disorder or disease is chemotherapy-induced nausea and vomiting (CINV).

Aspect 46. A method of treating chemotherapy-induced nausea and vomiting (CINV) in a patient in need of such treatment comprising administering to the patient an effective amount of at least one compound according to any one of aspects 1 to 22 or a pharmaceutical composition according to any one of aspects 23 to 25 in combination with an effective amount of at least one serotonin 5-HT$_3$ receptor antagonist and/or at least one glucocorticoid.

Aspect 47. The method according to aspect 44, wherein administering comprises orally administering.

Aspect 48. The method according to aspect 46, wherein administering comprises administering intravenously.

Aspect 49. The method according to any one of aspects 46 to 48, wherein the compound is the compound according to claim 22 or a pharmaceutically acceptable salt thereof, or the pharmaceutical composition is according to any one of claims 23 to 25, wherein the compound is the compound according to claim 22 or a pharmaceutically acceptable salt thereof; and wherein the serotonin 5-HT$_3$ receptor antagonist is ondansetron and/or granisetron, and the glucocorticoid is dexamethasone, or a pharmaceutically acceptable salt of the foregoing.

EXAMPLES

It should be noted that embodiments of the present invention described in detail below are exemplary for explaining the present invention only, and not be construed as limiting the present invention. Examples without a specific technology or condition can be implemented according to technology or condition in the documentation of the art or according to the product instructions. The reagents or instruments without manufacturers are available through conventional purchase. Those having skill in the art will recognize that the starting materials may be varied and additional steps employed to produce compounds encompassed by the present inventions, as demonstrated by the following examples.

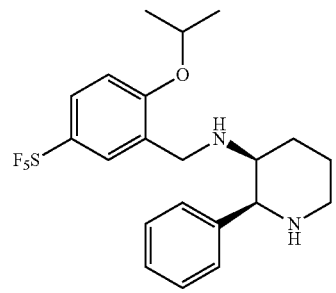

III

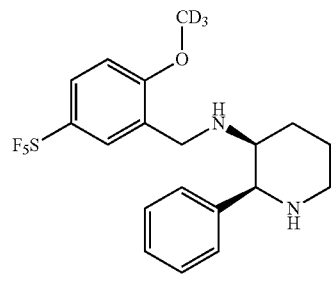

IV

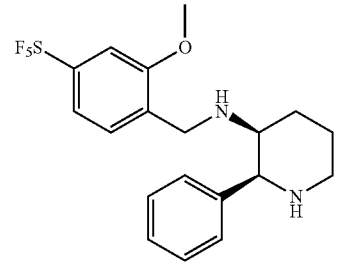

V

Example 1

(2S,3S)—N-(2-methoxy-5-(pentafluorosulfanyl)benzyl)-2-phenylpiperidin-3-amine (I)

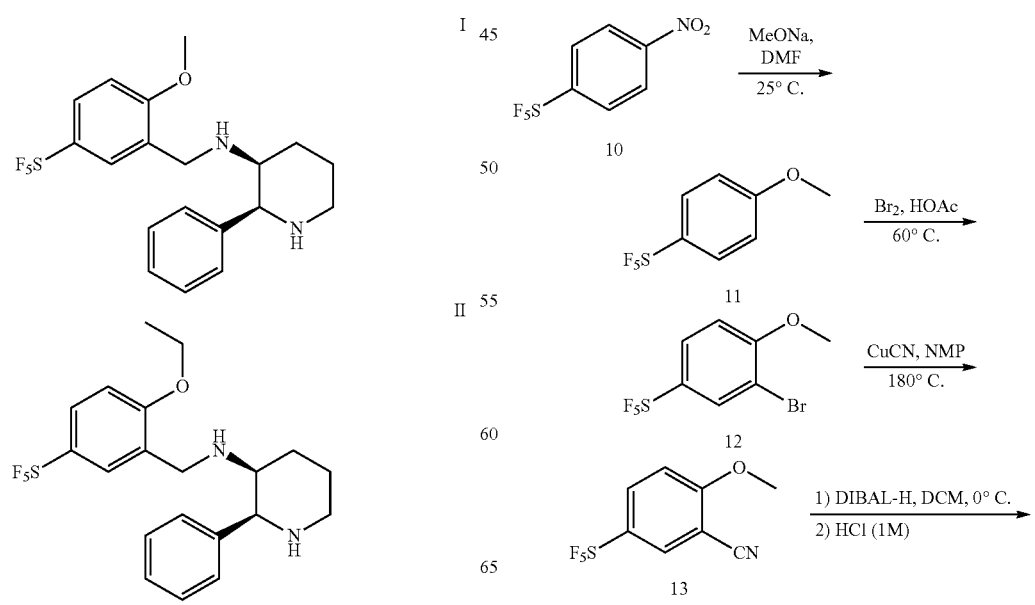

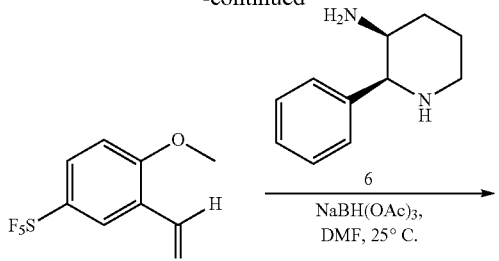

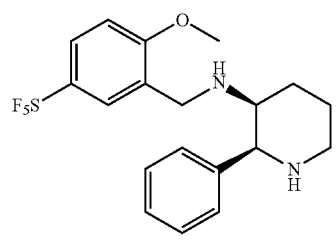

Step 1: 1-methoxy-4-(pentafluorosulfanyl)benzene (11)

To a stirred solution of 1-nitro-4-(pentafluorosulfanyl)benzene (10) (5.0 g, 20.1 mmol) in DMF (50 mL) at 25° C. was added MeONa (5.4 g, 100.5 mmol) in portions. The reaction was stirred at 25° C. for 0.5 h and then quenched with water (200 mL). The resulting mixture was extracted with EA (2×100 mL). The combined organic phase was washed with brine (2×100 mL), dried over anhydrous MgSO$_4$, filtered and concentrated. The residue was purified by column chromatography (silica gel, PE) to afford the titled compound 11 (3.0 g, 64%) as a colorless oil. $^1$H NMR (400 MHz, CDCl$_3$) δ=7.68 (d, J=9.2 Hz, 2H), 6.91 (d, J=8.8 Hz, 2H), 3.85 (s, 3H).

Step 2: 2-bromo-1-methoxy-4-(pentafluorosulfanyl)benzene (12)

To a stirred solution of 1-methoxy-4-(pentafluorosulfanyl)benzene (11) (3.0 g, 12.8 mmol) in HOAc (30 mL) was added Br$_2$ (10.2 g, 64.1 mmol) at 25° C. The reaction was stirred at 60° C. for 16 h. The reaction mixture was evaporated, the residue was purified by column chromatography (silica gel, PE) to afford the titled compound 12 (3.9 g, 98%) as a pale-yellow oil. $^1$H NMR (400 MHz, CDCl$_3$) δ=7.95 (d, J=2.4 Hz, 1H), 7.69 (dd, J=2.4, 9.2 Hz, 1H), 6.91 (d, J=9.2 Hz, 1H), 3.95 (s, 3H).

Step 3: 2-methoxy-5-(pentafluorosulfanyl)benzonitrile (13)

To a stirred solution of 2-bromo-1-methoxy-4-(pentafluorosulfanyl)benzene (12) (3.9 g, 12.5 mmol) in NMP (40 mL) was added CuCN (2.2 g, 24.9 mmol) at 25° C. in one portion. The reaction was heated to 170-180° C. under N$_2$ atmosphere for 4 h and then cooled to 25° C. The resulting mixture was diluted with water (100 mL) and extracted with EA (2×40 mL). The combined organic phase was washed with brine (40 mL), dried over anhydrous Na$_2$SO$_4$, filtered and concentrated. The residue was purified by column chromatography (silica gel, PE/EA=20:1-5:1) to afford the titled compound 13 (2.5 g, 78%) as a yellow solid. $^1$H NMR (400 MHz, CD$_3$OD) δ=8.18 (d, J=2.8 Hz, 1H), 8.10 (dd, J=2.6, 9.4 Hz, 1H), 7.34 (d, J=9.2 Hz, 1H), 4.05 (s, 3H).

Step 4: 2-methoxy-5-(pentafluorosulfanyl)benzaldehyde (14)

To a solution of 2-methoxy-5-(pentafluorosulfanyl)benzonitrile (13) (2.5 g, 9.7 mmol) in toluene (25 mL) was added DIBAL-H (7.7 mL, 11.6 mmol, 1.5 M in toluene) dropwise under N$_2$ atmosphere at 0° C. The reaction was stirred at 25° C. for 1 h and then quenched with aqueous HCl solution (20 mL, 1 M). The reaction mixture was extracted with EA (2×20 mL), the combined organic phase was washed with brine (20 mL), dried over anhydrous Na$_2$SO$_4$, filtered and concentrated. The residue was purified by column chromatography (silica gel, PE/EA=100:1-10:1) to afford the titled compound 14 (2.4 g, 96%) as a pale-yellow solid. $^1$H NMR (400 MHz, CDCl$_3$) δ=10.45 (s, 1H), 8.22 (d, J=2.8 Hz, 1H), 7.93 (dd, J=3.2, 9.2 Hz, 1H), 7.06 (d, J=9.2 Hz, 1H), 4.02 (s, 3H).

Step 5: (2S,3S)—N-(2-methoxy-5-(pentafluorosulfanyl)benzyl)-2-phenylpiperidin-3-amine (I)

To a stirred solution of 2-methoxy-5-(pentafluorosulfanyl)benzaldehyde (14) (0.9 g, 3.4 mmol) and (2S,3S)-2-phenylpiperidin-3-amine (6) (0.9 g, 5.2 mmol) in DMF (20 mL) was added NaBH(OAc)$_3$ (3.6 g, 17.2 mmol) in portions. The reaction was stirred at 25° C. for 2 h and then quenched with saturated aqueous NaHCO$_3$ solution slowly until pH >8. The resulting mixture was extracted with EA (2×40 mL). The combined organic phase was washed with brine (2×40 mL), dried over anhydrous Na$_2$SO$_4$, filtered and concentrated. The residue was purified by prep-HPLC to afford the titled compound I (0.8 g, 55%) as a white solid. $^1$H NMR (400 MHz, CD$_3$OD) δ=7.87 (dd, J=2.8, 9.2 Hz, 1H), 7.77 (d, J=2.4 Hz, 1H), 7.72 (d, J=7.2 Hz, 2H), 7.64-7.46 (m, 3H), 7.11 (d, J=9.2 Hz, 1H), 5.03 (d, J=3.2 Hz, 1H), 4.19 (d, J=12.8 Hz, 1H), 4.08 (s, 1H), 3.86 (s, 3H), 3.81 (d, J=13.2 Hz, 1H), 3.67 (d, J=12.4 Hz, 1H), 3.38-3.34 (m, 1H), 2.58-2.39 (m, 2H), 2.38-2.23 (m, 1H), 2.07-1.95 (m, 1H); MS (ESI): [M+H$^+$]=422.9.

Example 2

(2S,3S)—N-(2-ethoxy-5-(pentafluorosulfanyl)benzyl)-2-phenylpiperidin-3-amine (II)

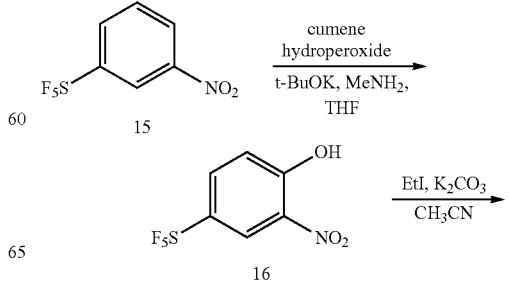

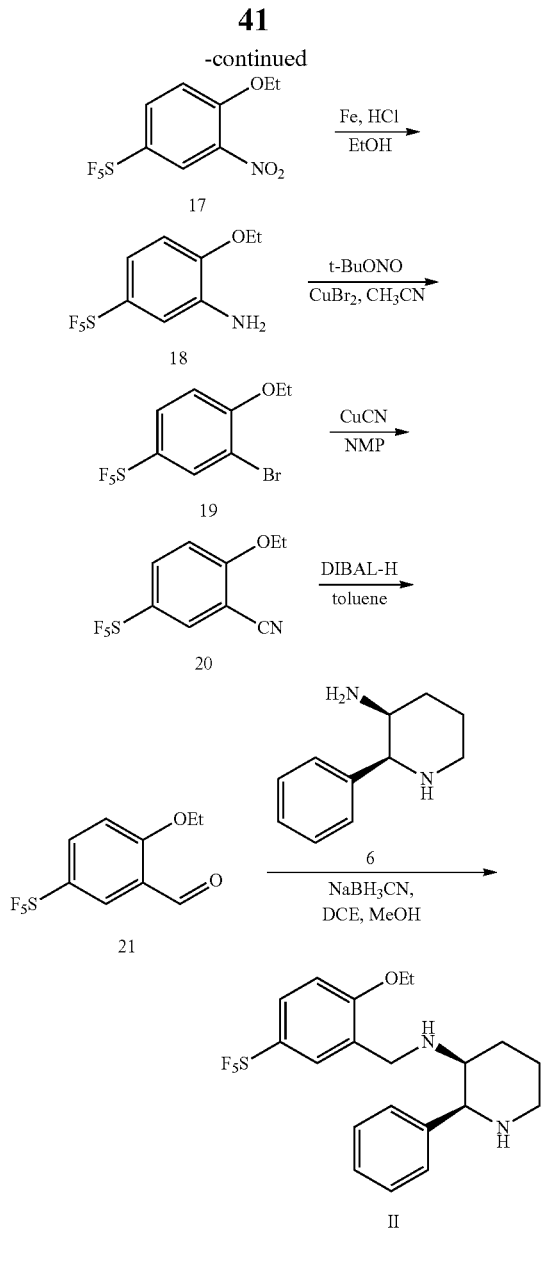

Step 1: 2-nitro-4-(pentafluorosulfanyl)phenol (16)

To a stirred slurry of t-BuOK (4.2 g, 36.0 mmol) in MeNH$_2$ (90 mL, 180 mmol, 2 M in THF) under N$_2$ atmosphere was added a solution of 1-nitro-3-(pentafluorosulfanyl)benzene (15) (3.0 g, 12.0 mmol) and cumene hydroperoxide (2.4 g, 13.2 mmol) in dry THF (30 mL) dropwise at −78° C. The reaction was stirred at −50° C. for 0.5 h and then warmed to 25° C. The reaction mixture was quenched with aqueous HCl solution (6 M) until pH<7, followed by extraction with EA (2×30 mL). The combined organic phase was washed with brine (30 mL), dried over anhydrous Na$_2$SO$_4$, filtered and concentrated. The residue was purified by column chromatography (silica gel, PE/EA=100% PE-100:1) to afford the titled compound 16 (3.0 g, 91%) as a yellow oil. $^1$H NMR (400 MHz, CDCl$_3$) δ=10.79 (br. s., 1H), 8.57 (d, J=2.8 Hz, 1H), 7.96 (dd, J=2.6, 9.2 Hz, 1H), 7.31-7.26 (m, 1H).

Step 2: 1-ethoxy-2-nitro-4-(pentafluorosulfanyl)benzene (17)

To a stirred solution of 2-nitro-4-(pentafluorosulfanyl)phenol (16) (0.5 g, 1.9 mmol) and iodoethane (0.6 g, 3.8 mmol) in CH$_3$CN (5 mL) was added K$_2$CO$_3$ (0.6 g, 4.7 mmol). The reaction was heated under reflux in the sealed tube for 16 h, filtered and concentrated. The residue was purified by column chromatography (silica gel, PE/EA=100% PE-50:1) to afford the titled compound 17 (342 mg, 62%) as a yellow solid. $^1$H NMR (400 MHz, CDCl$_3$) δ=8.26 (d, J=2.8 Hz, 1H), 7.90 (dd, J=2.8, 9.2 Hz, 1H), 7.12 (d, J=9.2 Hz, 1H), 4.26 (q, J=7.2 Hz, 2H), 1.51 (t, J=7.0 Hz, 3H).

Step 3: 2-ethoxy-5-(pentafluorosulfanyl)aniline (18)

To a stirred solution of 1-ethoxy-2-nitro-4-(pentafluorosulfanyl)benzene (17) (340 mg, 1.2 mmol) in EtOH (3 mL) and concentrated HCl (3 mL) was added Fe powder (0.2 g, 3.5 mmol) in portions at 25° C. The reaction was heated under reflux for 3 h and then concentrated. The residue was dissolved in water (10 mL) and extracted with EA (2×15 mL). The combined organic phase was washed with brine (10 mL), dried over anhydrous Na$_2$SO$_4$, filtered and concentrated to afford the titled compound 18 (0.3 g, 98%) as an off-white solid. MS (ESI): [M+H+CH$_3$CN]$^+$=304.8.

Step 4: 2-bromo-1-ethoxy-4-(pentafluorosulfanyl)benzene (19)

To a stirred slurry of 2-ethoxy-5-(pentafluorosulfanyl)aniline (18) (0.3 g, 1.1 mmol) and CuBr$_2$ (255 mg, 1.1 mmol) in CH$_3$CN (3 mL) was added t-BuONO (0.3 g, 2.9 mmol) dropwise at 25° C. The reaction was stirred at 25° C. for 0.5 h and then concentrated. The residue was purified by column chromatography (silica gel, PE/EA=100:1) to afford the titled compound 19 (240 mg, 64%) as a colorless oil. $^1$H NMR (400 MHz, CDCl$_3$) δ=7.94 (d, J=2.4 Hz, 1H), 7.66 (dd, J=2.4, 9.2 Hz, 1H), 6.88 (d, J=9.2 Hz, 1H), 4.16 (q, J=7.2 Hz, 2H), 1.50 (t, J=7.2 Hz, 3H).

Step 5: 2-ethoxy-5-(pentafluorosulfanyl)benzonitrile (20)

To a stirred solution of 2-bromo-1-ethoxy-4-(pentafluorosulfanyl)benzene (19) (180 mg, 0.55 mmol) in NMP (2 mL) was added CuCN (0.1 g, 1.1 mmol) in one portion. The reaction was heated to 160° C. for 4 h under N$_2$ atmosphere and then cooled to 25° C. The reaction mixture was diluted with water (5 mL) and extracted with EA (2×3 mL). The combined organic phase was washed with brine (3 mL), dried over anhydrous Na$_2$SO$_4$, filtered and concentrated. The residue was purified by column chromatography (silica gel, PE/EA=100:1-5:1) to afford the titled compound 20 (120 mg, 80%) as a colorless oil. $^1$H NMR (400 MHz, CDCl$_3$) δ=7.96 (d, J=2.8 Hz, 1H), 7.90 (dd, J=2.8, 9.2 Hz, 1H), 7.00 (d, J=9.2 Hz, 1H), 4.23 (q, J=6.8 Hz, 2H), 1.52 (t, J=7.2 Hz, 3H).

Step 6: 2-ethoxy-5-(pentafluorosulfanyl)benzaldehyde (21)

To a stirred solution of 2-ethoxy-5-(pentafluorosulfanyl)benzonitrile (20) (120 mg, 0.44 mmol) in toluene (1 mL)

was added DIBAL-H (0.4 mL, 0.6 mmol, 1.5 M in toluene) dropwise at 0° C. The reaction was stirred and warmed to 25° C. over 1 h. The reaction mixture was quenched with aqueous HCl solution (1 mL, 6 M) and then extracted with EA (2×2 mL). The combined organic phase was washed with brine (2 mL), dried over anhydrous $Na_2SO_4$, filtered and concentrated. The residue was purified by column chromatography (silica gel, PE/EA=100:1-5:1) to afford the titled compound 21 (77 mg, 64%) as a colorless oil. $^1$H NMR (400 MHz, $CDCl_3$) δ=10.47 (s, 1H), 8.22 (d, J=2.8 Hz, 1H), 7.89 (dd, J=2.8, 9.2 Hz, 1H), 7.03 (d, J=9.2 Hz, 1H), 4.23 (d, J=6.8 Hz, 2H), 1.52 (t, J=7.0 Hz, 3H).

Step 7: (2S,3S)—N-(2-ethoxy-5-(pentafluorosulfanyl)benzyl)-2-phenylpiperidin-3-amine (II)

To a stirred solution of 2-ethoxy-5-(pentafluorosulfanyl)benzaldehyde (21) (40 mg, 0.1 mmol) in DCE (0.5 mL) was added (2S,3S)-2-phenylpiperidin-3-amine (6) (31 mg, 0.18 mmol). The reaction mixture was stirred at 25° C. for 0.5 h. After that, $NaBH_3CN$ (11 mg, 175 μmop, MeOH (0.5 mL) and AcOH (0.1 mL) was added in one potion. The resulting mixture was stirred at 25° C. for 1 h and then concentrated. The residue was purified by prep-HPLC to afford the titled compound II (23 mg, 31%) as a white solid. $^1$H NMR (400 MHz, $CD_3OD$) δ=7.72 (d, J=8.4 Hz, 1H), 7.63 (s, 1H), 7.57-7.24 (m, 5 H), 6.99 (d, J=8.8 Hz, 1H), 4.79-4.53 (m, 2H), 4.09-3.80 (m, 3H), 3.67-3.49 (m, 2H), 3.22 (t, J=12.0 Hz, 1H), 2.39-2.19 (m, 2H), 2.11-1.97 (m, 1H), 1.87 (d, J=12.0 Hz, 1H), 1.33-1.09 (m, 3H); MS (ESI): [M+H]$^+$=436.9.

Example 3

(2S,3S)—N-(2-isopropoxy-5-(pentafluorosulfanyl)benzyl)-2-phenylpiperidin-3-amine (III)

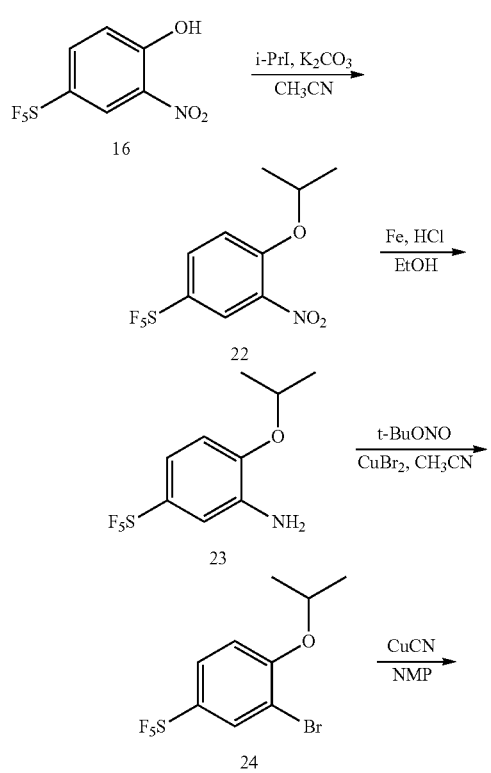

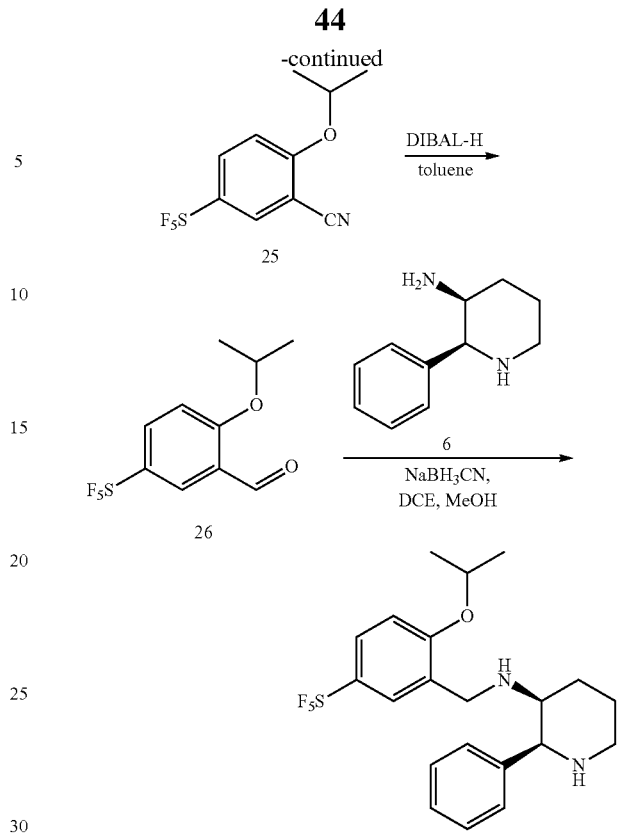

Step 1: 1-isopropoxy-2-nitro-4-(pentafluorosulfanyl)benzene (22)

To a stirred solution of 2-nitro-4-(pentafluorosulfanyl)phenol (16) (0.5 g, 1.9 mmol) and 2-iodopropane (0.6 g, 3.8 mmol) in $CH_3CN$ (5 mL) in a sealed tube was added $K_2CO_3$ (0.6 g, 4.7 mmol). The reaction was heated under reflux in a sealed tube for 16 h, filtered and concentrated. The residue was purified by column chromatography (silica gel, PE/EA=100:0-50:1) to afford the titled compound 22 (0.2 g, 35%) as a yellow solid. $^1$H NMR (400 MHz, $CDCl_3$) δ=8.21 (d, J=2.8 Hz, 1H), 7.87 (dd, J=2.4, 9.2 Hz, 1H), 7.12 (d, J=9.2 Hz, 1H), 4.84-4.71 (m, 1H), 1.44 (d, J=6.0 Hz, 6H).

Step 2: 2-isopropoxy-5-(pentafluorosulfanyl)aniline (23)

To a stirred solution of 1-isopropoxy-2-nitro-4-(pentafluorosulfanyl)benzene (22) (0.2 g, 0.65 mmol) in EtOH (2 mL) and concentrated HCl (0.5 mL) was added Fe powder (109 mg, 2.0 mmol) in portions at 25° C. The resulting mixture was heated to reflux for 3 h and then concentrated. The residue was dissolved in water (5 mL) and extracted with EA (2×5 mL). The combined organic phase was washed with brine (5 mL), dried over anhydrous $Na_2SO_4$, filtered and concentrated to afford the titled compound 23 (0.2 g, crude) as an off-white solid. The crude product was used for next step without further purification. MS (ESI): [M+H+$CH_3CN$]$^+$=318.8.

Step 3: 2-bromo-1-isopropoxy-4-(pentafluorosulfanyl)benzene (24)

To a stirred slurry of 2-isopropoxy-5-(pentafluorosulfanyl)aniline (23) (0.2 g, 0.7 mmol) and $CuBr_2$ (161 mg, 0.7 mmol) in CH₃CN (2 mL) was added t-BuONO (186 mg, 1.8 mmol) dropwise at 25° C. The reaction was stirred at 25° C. for 1 h and then concentrated. The residue was purified by column chromatography (silica gel, PE/EA=100:1) to afford the titled compound 24 (150 mg, 61%) as a colorless oil.

Step 4: 2-isopropoxy-5-(pentafluorosulfanyl)benzonitrile (25)

To a stirred solution of 2-bromo-1-isopropoxy-4-(pentafluorosulfanyl)benzene (24) (70 mg, 0.2 mmol) in NMP (1 mL) was added CuCN (37 mg, 0.4 mmol) in one portion. The reaction was heated to 160° C. for 4 h under N₂ atmosphere and then cooled to 25° C. The resulting mixture was diluted with water (5 mL) and extracted with EA (2×2 mL). The combined organic phase was washed with brine (2 mL), dried over anhydrous Na₂SO₄, filtered and concentrated. The residue was purified by column chromatography (silica gel, PE/EA=100:1-5:1) to afford the titled compound 25 (25 mg, 42%) as a colorless oil. $^1$H NMR (400 MHz, CDCl₃) δ=7.95 (d, J=2.4 Hz, 1H), 7.88 (dd, J=2.4, 9.2 Hz, 1H), 6.99 (d, J=9.2 Hz, 1H), 4.76-4.70 (m, 1H), 1.44 (d, J=6.4 Hz, 6H).

Step 5: 2-isopropoxy-5-(pentafluorosulfanyl)benzaldehyde (26)

To a stirred solution of 2-isopropoxy-5-(pentafluorosulfanyl)benzonitrile (25) (25 mg, 87 μmop in toluene (0.5 mL) was added DIBAL-H (70 μL, 0.1 mmol, 1.5 M in toluene) dropwise at 0° C. The reaction was stirred and warmed up to 25° C. over 1 h. The reaction was quenched with aqueous HCl solution (2 mL, 6 M) and then extracted with EA (2×2 mL). The combined organic phase was washed with brine (2 mL), dried over anhydrous Na₂SO₄, filtered and concentrated. The residue was purified by column chromatography (silica gel, PE/EA=100:1-5:1) to afford the titled compound 26 (18 mg, 71%) as a white solid.

Step 6: (2S,3S)—N-(2-isopropoxy-5-(pentafluorosulfanyObenzyl)-2-phenylpiperidin-3-amine (III)

To a stirred solution of 2-isopropoxy-5-(pentafluorosulfanyl)benzaldehyde (26) (18 mg, 62 μmop in DCE (0.5 mL) was added (2S,3S)-2-phenylpiperidin-3-amine (6) (14 mg, 80 μmol). The reaction mixture was stirred at 25° C. for 0.5 h. After that, NaBH₃CN (5 mg, 80 μmop, MeOH (0.5 mL) and AcOH (0.1 mL) was added. The resulting solution was stirred at 25° C. for 1 h and then quenched with saturated aqueous NaHCO₃ solution (2 mL). The resulting mixture was extracted with EA (2×2 mL). The combined organic phase was washed with brine (2 mL), dried over anhydrous MgSO₄, filtered and concentrated. The residue was treated with concentrated HCl (0.1 mL) in CH₃CN (2 mL). After concentration, the resulting solid was triturated with CH₃CN (2 mL) and filtered to afford the titled compound III (15 mg, 46%) as an off-white solid. $^1$H NMR (400 MHz, CD₃OD) δ=7.86-7.74 (m, 2H), 7.62 (d, J=4.0 Hz, 2H), 7.51 (dd, J=1.6, 5.0 Hz, 3H), 7.08 (d, J=9.2 Hz, 1H), 4.95-4.91 (m, 1H), 4.71-4.67 (m, 1H), 4.09 (d, J=13.6 Hz, 1H), 3.92 (s, 1H), 3.78 (d, J=13.2 Hz, 1H), 3.65 (d, J=12.4 Hz, 1H), 3.29-3.24 (m, 1H), 2.51-2.35 (m, 2H), 2.32-2.19 (m, 1H), 2.03-1.93 (m, 1H), 1.31 (dd, J=6.0, 18.0 Hz, 6H); MS (ESI): [M+H]⁺=450.9.

Example 4

(2S,3S)—N-(2-(methoxy-d₃)-5-(pentafluorosulfanyl)benzyl)-2-phenylpiperidin-3-amine (IV)

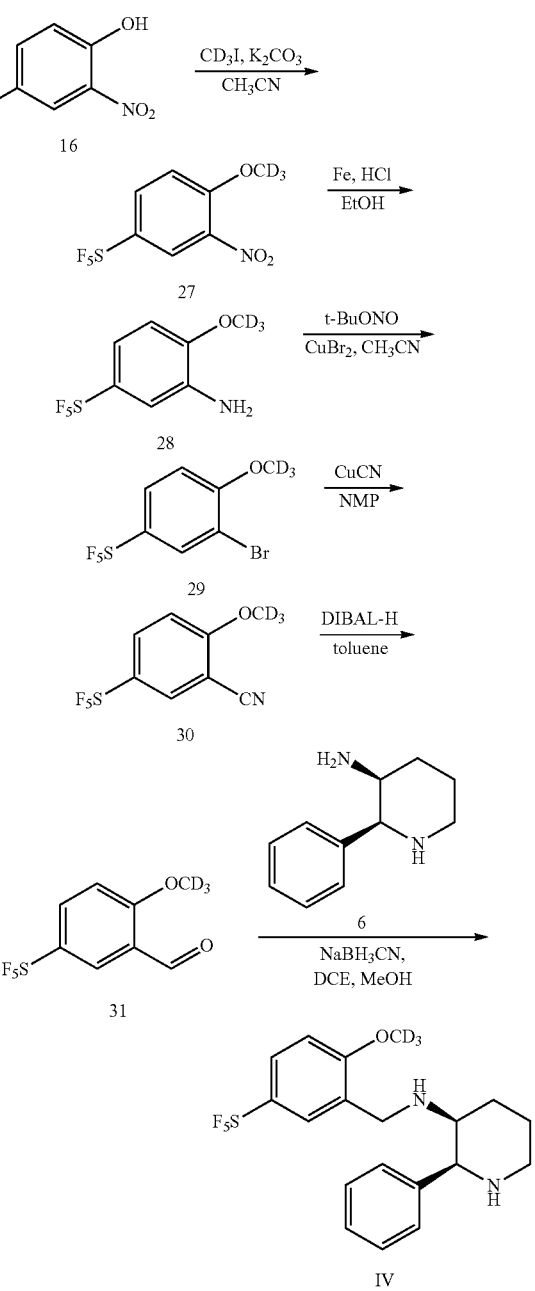

Step 1: pentafluoro(4-(methoxy-d₃)-3-nitrophenyl)sulfane (27)

To a stirred solution of 2-nitro-4-(pentafluorosulfanyl) phenol (16) (2.0 g, 7.5 mmol) and iodomethane-d₃ (2.2 g, 15.1 mmol) in CH₃CN (20 mL) was added K₂CO₃ (2.6 g, 18.9 mmol). The reaction was heated under reflux in a sealed tube for 16 h. After that, the reaction mixture was filtered and concentrated. The residue was purified by column chromatography (silica gel, PE/EA=100:1-50:1) to afford the titled compound 27 (1.8 g, 71%) as a yellow solid. $^1$H NMR (400 MHz, CDCl$_3$) δ=8.29 (d, J=2.4 Hz, 1H), 7.94 (dd, J=2.8, 9.2 Hz, 1H), 7.15 (d, J=9.2 Hz, 1H).

Step 2: 2-(methoxy-d$_3$)-5-(pentafluorosulfanyl)aniline (28)

To a stirred solution of pentafluoro(4-(methoxy-d$_3$)-3-nitrophenyl)sulfane (27) (1.4 g, 5.0 mmol) in EtOH (15 mL) and concentrated HCl (5 mL) was added Fe powder (0.8 g, 14.9 mmol) in portions at 25° C. The resulting slurry was heated to reflux for 3 h and then concentrated. The residue was dissolved in water (20 mL) and extracted with EA (2×20 mL). The combined organic phase was washed with brine (20 mL), dried over anhydrous Na$_2$SO$_4$, filtered and concentrated to afford the titled compound 28 (1.3 g, crude) as an off-white solid. The crude product was used for next step without further purification. MS (ESI): [M+H+CH$_3$CN]$^+$= 293.8.

Step 3: (3-bromo-4-(methoxy-d$_3$)phenyl)pentafluorosulfane (29)

To a stirred slurry of 2-(methoxy-d$_3$)-5-(pentafluorosulfanyl)aniline (28) (1.3 g, 5.2 mmol) and CuBr$_2$ (1.2 g, 5.2 mmol) in CH$_3$CN (20 mL) was added t-BuONO (1.3 g, 12.9 mmol) dropwise at 25° C. The reaction was stirred at 25° C. for 1 h and then concentrated. The residue was purified by column chromatography (silica gel, PE/EA=100:1) to afford the titled compound 29 (1.5 g, 92%) as a colorless oil.

Step 4: 2-(methoxy-d$_3$)-5-(pentafluorosulfanyl)benzonitrile (30)

To a stirred solution of (3-bromo-4-(methoxy-d$_3$)phenyl)pentafluorosulfane (29) (1.5 g, 4.8 mmol) in NMP (20 mL) was added CuCN (0.9 g, 9.5 mmol) in one portion. The reaction was heated to 160° C. for 4 h under N$_2$ atmosphere and then cooled to 25° C. The resulting mixture was diluted with water (40 mL) and extracted with EA (2×20 mL). The combined organic phase was washed with brine (20 mL), dried over anhydrous Na$_2$SO$_4$, filtered and concentrated. The residue was purified by column chromatography (silica gel, PE/EA=100:1-5:1) to afford the titled compound 30 (1.0 g, 80%) as an off-white solid. $^1$H NMR (400 MHz, CDCl$_3$) δ=8.05-7.86 (m, 2H), 7.02 (d, J=9.2 Hz, 1H).

Step 5: 2-(methoxy-d$_3$)-5-(pentafluorosulfanyl)benzaldehyde (31)

To a stirred solution of 2-(methoxy-d$_3$)-5-(pentafluorosulfanyl)benzonitrile (30) (0.9 g, 3.4 mmol) in DCM (10 mL) was added DIBAL-H (6.9 mL, 6.9 mmol, 1 M in hexane) dropwise at 0° C. The reaction was stirred at 0-25° C. for 2 h and then poured into aqueous HCl solution (20 mL, 1 M). The resulting mixture was extracted with EA (2×10 mL). The combined organic phase was washed with brine (10 mL), dried over anhydrous Na$_2$SO$_4$, filtered and concentrated. The residue was purified by column chromatography (silica gel, PE/EA=20:1-5:1) to afford the titled compound 31 (0.7 g, 54%) as an off-white solid. $^1$H NMR (400 MHz, CDCl$_3$) δ=10.45 (s, 1H), 8.23 (d, J=3.2 Hz, 1H), 8.01-7.88 (m, 1 H), 7.10-6.99 (m, 1H).

Step 6: (2S,3S)—N-(2-(methoxy-d$_3$)-5-(pentafluorosulfanyl)benzyl)-2-phenylpiperidin-3-amine (IV)

To a stirred solution of 2-(methoxy-d$_3$)-5-(pentafluorosulfanyl)benzaldehyde (31) (0.49 g, 1.8 mmol) in DCE (7 mL) was added (2S,3S)-2-phenylpiperidin-3-amine (6) (0.4 g, 2.3 mmol) in one portion. The reaction was stirred at 25° C. for 1 h and then followed by addition of NaBH$_3$CN (242 mg, 3.9 mmol), MeOH (7 mL) and AcOH (1 mL). The reaction was stirred at 25° C. for 2 h and then quenched with saturated aqueous NaHCO$_3$ solution (20 mL). The resulting mixture was extracted with EA (2×15 mL). The combined organic phase was washed with brine (15 mL), dried over anhydrous MgSO$_4$, filtered and concentrated. The residue was dissolved in CH$_3$CN (10 mL) and treated with concentrated HCl (5 mL). The solution was evaporated to dryness. The resulting solid was triturated with CH$_3$CN (5 mL) and filtered to afford the titled compound IV (0.6 g, 76%) as an off-white solid. $^1$H NMR (400 MHz, CD$_3$OD) δ=7.86 (dd, J=2.4, 9.2 Hz, 1H), 7.81-7.65 (m, 3H), 7.63-7.44 (m, 3H), 7.10 (d, J=9.2 Hz, 1H), 5.03 (d, J=2.8 Hz, 1H), 4.19 (d, J=12.8 Hz, 1H), 4.08 (s, 1H), 3.81 (d, J=13.2 Hz, 1H), 3.67 (d, J=12.0 Hz, 1H), 3.39-3.33 (m, 1H), 2.56-2.39 (m, 2H), 2.37-2.23 (m, 1H), 2.08-1.95 (m, 1H); MS (ESI): [M+H]$^+$= 426.0.

Example 5

(2S,3S)—N-(2-methoxy-4-(pentafluorosulfanyl)benzyl)-2-phenylpiperidin-3-amine (V)

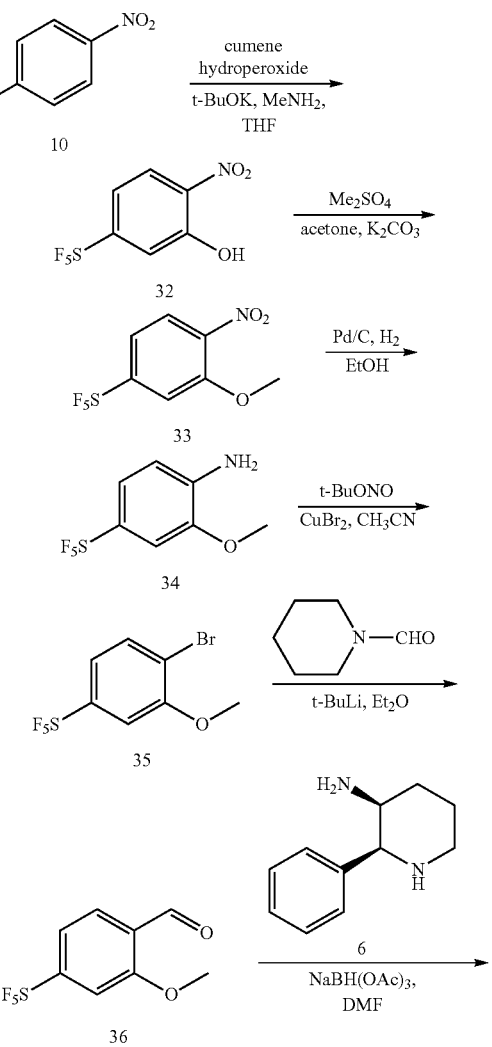

-continued

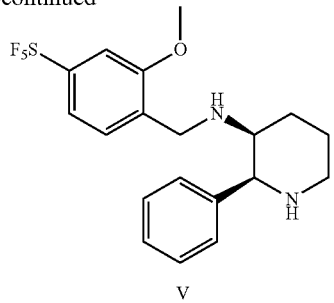

V

Step 1: 2-nitro-5-(pentafluorosulfanyl)phenol (32)

To a stirred slurry of t-BuOK (1.4 g, 12.0 mmol) in MeNH₂ (30 mL, 60 mmol, 2 M in THF) was added a solution of 1-nitro-4-(pentafluorosulfanyl)benzene (10) (1.0 g, 4.0 mmol) and cumene hydroperoxide (0.8 g, 4.4 mmol) in dry THF (10 mL) dropwise at −78° C. The reaction was stirred at −50° C. for 0.5 h, and was gradually warmed to 25° C. The reaction mixture was cooled down and quenched with aqueous HCl solution (60 mL, 1 M) at −10° C., extracted with EA (2×60 mL). The combined organic phase was washed with brine (50 mL), dried over anhydrous Na₂SO₄, filtered and concentrated. The residue was purified by column chromatography (silica gel, PE/EA=100:1-3:1) to afford the titled compound 32 (1.0 g, 91%) as a yellow oil. $^1$H NMR (400 MHz, CDCl₃) δ=10.56 (s, 1H), 8.23 (d, J=9.6 Hz, 1H), 7.62 (d, J=2.4 Hz, 1H), 7.39 (s, J=2.4, 9.6 Hz, 1H).

Step 2: 2-methoxy-1-nitro-4-(pentafluorosulfanyl)benzene (33)

To a stirred solution of 2-nitro-5-(pentafluorosulfanyl)phenol (32) (0.8 g, 3.0 mmol) and Me₂SO₄ (0.5 g, 3.9 mmol) in acetone (20 mL) was added K₂CO₃ (0.8 g, 6.0 mmol) in one portion. The reaction was heated under reflux for 1 h and then quenched with water (40 mL). The resulting mixture was extracted with EA (2×30 mL). The combined organic phase was washed with brine (30 mL), dried over anhydrous Mg₂SO₄, filtered and concentrated to afford the titled compound 33 (0.8 g, 95%) as a yellow oil. $^1$H NMR (400 MHz, CDCl₃) δ=7.89 (d, J=9.2 Hz, 1H), 7.49-7.42 (m, 2H), 4.03 (s, 3H).

Step 3: 2-methoxy-4-(pentafluorosulfanyl)aniline (34)

To a stirred solution of 2-methoxy-1-nitro-4-(pentafluorosulfanyl)benzene (33) (1.0 g, 3.6 mmol) in MeOH (20 mL) was added Pd/C (0.1 g, 10%). The reaction was charged with H₂ balloon and stirred at 25° C. for 24 h. After that, the reaction mixture was filtered, the filtrate was concentrated to afford the titled compound 34 (0.8 g, 90%) as an off-white solid. $^1$H NMR (400 MHz, CDCl₃) δ=7.21 (dd, J=2.2, 8.8 Hz, 1H), 7.12 (d, J=2.2 Hz, 1H), 6.65 (d, J=8.8 Hz, 1H), 3.89 (s, 3H).

Step 4: 1-bromo-2-methoxy-4-(pentafluorosulfanyl)benzene (35)

To a stirred slurry of t-BuONO (1.0 g, 10.0 mmol) and CuBr₂ (0.9 g, 4.0 mmol) in CH₃CN (10 mL) was added 2-methoxy-4-(pentafluorosulfanyl)aniline (34) (1.0 g, 4.0 mmol) in one portion at 0° C. The reaction was stirred at 25° C. for 0.5 h and then heated to reflux for 1 h. The resulting mixture was cooled to 25° C., quenched with saturated aqueous NH₄Cl solution (10 mL) and extracted with EA (2×10 mL). The combined organic phase was washed with brine (10 mL), dried over anhydrous MgSO₄, filtered and concentrated. The residue was purified by column chromatography (silica gel, PE/EA=100:1-10:1) to afford the titled compound 35 (1.0 g, 80%) as a white solid. $^1$H NMR (400 MHz, CD₃OD) δ=7.75 (d, J=8.8 Hz, 1H), 7.41 (d, J=2.4 Hz, 1H), 7.34 (dd, J=2.2, 8.8 Hz, 1H), 3.95 (s, 3H).

Step 5: 2-methoxy-4-(pentafluorosulfanyl)benzaldehyde (36)

To a stirred solution of 1-bromo-2-methoxy-4-(pentafluorosulfanyl)benzene (35) (0.4 g, 1.3 mmol) in Et₂O (4 mL) was added t-BuLi (1.7 mL, 2.2 mmol, 1.3 M in pentane) dropwise at −78° C. The resulting mixture was stirred at −78° C. for 0.5 h and then followed by the addition of piperidine-1-carbaldehyde (217 mg, 2.0 mmol) dropwise at −78° C. The reaction was stirred at −78° C. for 1 h and then quenched with saturated aqueous NH₄C₁ solution (5 mL). The reaction mixture was extracted with MTBE (2×10 mL). The combined organic phase was dried over anhydrous MgSO₄, filtered and concentrated to afford the titled compound 36 (0.3 g, 89%) as a yellow solid. $^1$H NMR (400 MHz, CDCl₃) δ=10.48 (s, 1H), 7.91 (d, J=8.8 Hz, 1H), 7.43 (d, J=8.8 Hz, 1H), 7.36 (s, 1H), 4.01 (s, 3H).

Step 6: (2S,3S)—N-(2-methoxy-4-(pentafluorosulfanyObenzyl)-2-phenylpiperidin-3-amine (V)

To a stirred solution of 2-methoxy-4-(pentafluorosulfanyl)benzaldehyde (36) (0.3 g, 1.1 mmol) and (2S,3S)-2-phenylpiperidin-3-amine (6) (0.2 g, 1.1 mmol) in DMF (3 mL) was added NaBH(OAc)₃ (0.7 g, 5.7 mmol) in portions at 25° C. The reaction was stirred for 4 h at 25° C. and then quenched with water (3 mL). The reaction mixture was extracted with EA (2×10 mL). The combined organic phase was washed with brine (10 mL), dried over anhydrous MgSO₄, filtered and concentrated. The residue was purified by prep-HPLC to afford the titled compound V (120 mg, 25%) as a white solid. $^1$HNMR (400 MHz, D₂O) δ=7.59-7.38 (m, 4H), 7.34 (d, J=8.4 Hz, 1H), 7.29-7.13 (m, 3H), 4.88 (d, J=3.6 Hz, 1H), 4.33 (d, J=13.6 Hz, 1H), 4.04 (d, J=13.6 Hz, 1H), 3.95 (d, J=4.0 Hz, 1H), 3.70-3.63 (m, 1H), 3.60 (s, 3H), 3.33-3.22 (m, 1H), 2.50-2.40 (m, 1H), 2.28-2.18 (m, 1H), 2.14-2.00 (m, 2H); MS (ESI): [M+H]⁺=423.3.

Example 6

Pharmacological Studies

In the example, the pharmacological properties are described in detail with the compound having formula I-V.

A. Inhibitory Effect of Compound I-V on Human NK-1 Receptor Using Binding Assay.

Figure 1B:
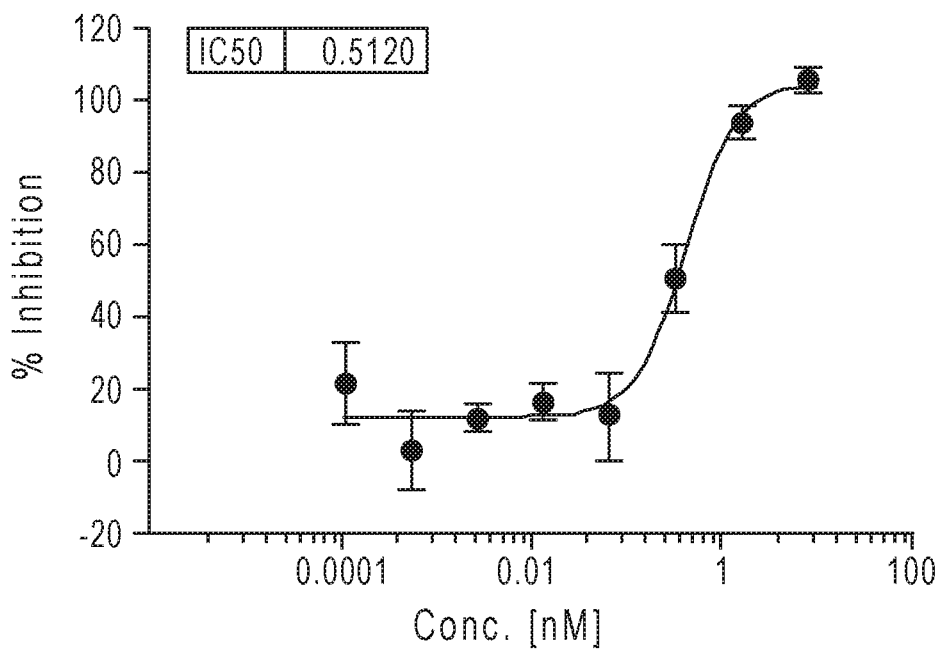

Human Tachykinin NK-1 receptor binding assay was performed using CisBio's Tag-Lite® Ligand binding assay. The homogeneous binding assay employees the time resolved fluorescence energy transfer (TR-FRET) technology. The potential inhibitory effect of Compound I and V on human NK-1 receptor was evaluated by TagLite® Tachykinin NK-1 receptor binding assay. The results are shown in the following Table 1, while the fitting dose-response curves for Compound I are shown in FIGS. 1A and 1B.

1. Tag-Lite® Tachykinin NK-1 receptor binding assay.

Materials: Tag-Lite® Tachykinin NK-1 labeled Cells, Tachykinin NK-1 Receptor red agonist Fluorescent Ligand (10 µM×50 µL), Tag-Lite Buffer (TLB) (5×concentration) (CisBio, Redford, Mass., U.S.A). [Sar9, Met(O2)11]-Substance P-Polypeptides (Tocris, Bristol, UK).

Experimental procedure for saturation binding ($K_d$ determination): Saturation binding assay measures total and non-specific binding of increasing concentrations of ligand under conditions of equilibrium. To perform the assay, the fluorescent ligand is titrated into a solution containing a fixed amount of Tag-Lite® Tachykinin NK-1 labeled cells. Prepare fluorescent ligand by diluting the Tachykinin NK-1 receptor red agonist stock solution (10000 nM) 10 µL to 240 µL 1× Tag-Lite Buffer (TLB) to obtain the highest concentration F1=400 nM for the saturation binding curve. Starting with the F1 solution (400 nM), ½ serial dilutions were prepared, and resulted 200-3.1 nM solutions. The Homogenous Time Resolved Fluorescence (HTRF) ratio obtained from this titration is the total binding. The fluorescent ligand was also titrated into a solution containing a fixed amount of labeled cells and a 100-fold molar excess of unlabeled ligand (40 uM), [Sar9, Met(O2)11]-Substance P-Polypeptides in DMSO. The HTRF ratio obtained from this titration is the non-specific binding The assay was performed in duplicate wells for each assay points and incubate all reagents for 2 h at room temperature, read the $Signal_{665nm}$ and $Signal_{620nm}$ using Evision. Data analysis was performed by calculating the Ratio following the formula below, total binding and nonspecific binding were analyzed with GraphPad Prism 5.0, and $K_d$ value was calculated.

$$Ratio = \frac{Signal\ 665\ nm}{Signal\ 620\ nm} \times 10^4$$

2. Competitive binding ($K_i$ determination): Competitive binding assay measures the dissociation constant, To perform the assay, the compound is titrated into a solution containing a fixed concentration of fluorescent ligand and a fixed amount of cells.

Experimental procedure for competitive binding ($K_i$ determination): Perform CisBio's Tag-Lite® Tachykinin NK-1 binding assay according to manufacturer's protocol. Briefly, prepare each test compound in 8 points of concentration. Dilute compound with 1×TLB to an initial concentration of 40 nM (C1). Starting with the C1 solution (40 nM), prepare ⅕ serial dilutions in 1×TLB by adding 10 µL C1 to 40 µL of 1×TLB, mix gently and repeat the ⅕ serial dilutions to prepare C2, C3, C4, C5, C6, C7, C8 solutions. For competition dose-response of compounds, the optimal fluorescent ligand concentration is the one that allows 50% $K_a$ of receptor binding. Add 5 µL of fluorescent ligand stock solution (10000 nM) to 1245 µL of 1×TLB, mix gently to obtain the 40 nM working solution. Competitive binding assay was run in duplicate for all assay points. Combine 10 µL labeled cells into each well; 5 µL compound dilutions (C1-C8) into each appropriate well; repeat for each compound tested, and 5 µL fluorescent ligand into each well. Incubate 2 h at room temperature, read the $Signal_{665nm}$ and $Signal_{620nm}$ using Evision. Data analysis was performed by calculating the Ratio following the formula below, the competitive binding data for each compound was analyzed with GraphPad Prism 5.0, and $IC_{50}$ value was calculated for each compound.

$$Ratio = \frac{Signal\ 665\ nm}{Signal\ 620\ nm} \times 10^4$$

3. Experimental results.

TABLE 1

| Data Summary of Competitive Binding Assay. | |
|---|---|
| Test Article | $IC_{50}$ on hNK-1 receptor[nM] |
| Compound I | 0.6398 |
| Compound V | 0.5120 |

B. Antagonist activity of Compound I-V on human NK-1, NK-2, NK-3 cell lines by Calcium Flux FLIPR assay.

Figure 2A:
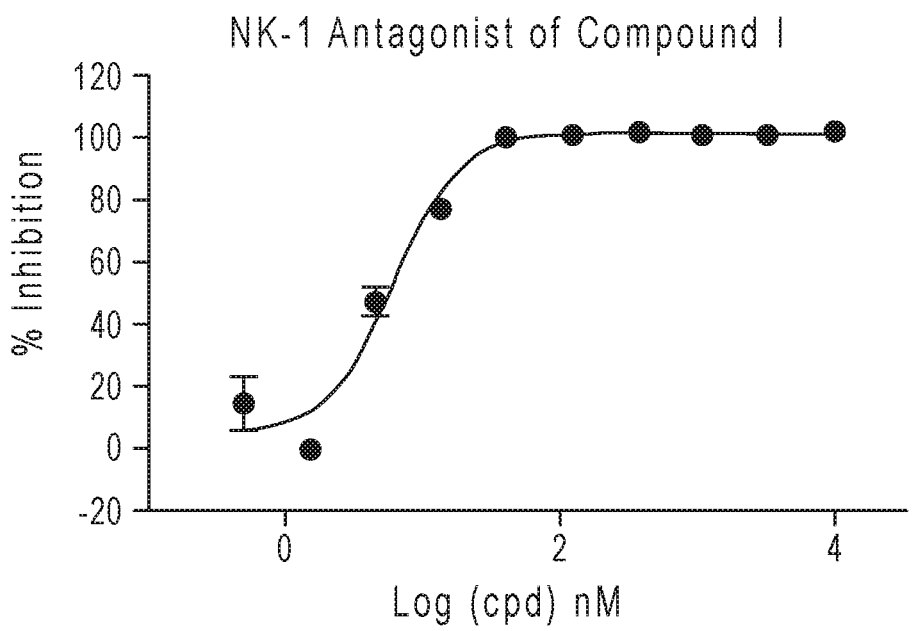
FIGS. 2A and 2B show NK-1/2/3 receptor antagonist activity of Compound I.
Figure 2B:
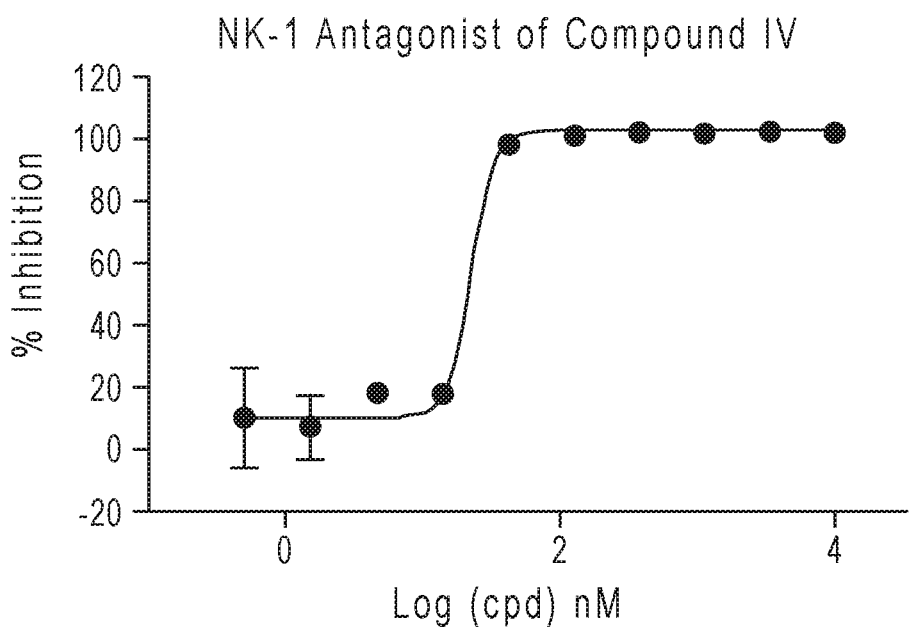

The potential antagonist activity of Compound I and IV on human NK-1/2/3 receptor was evaluated by calcium flux FLIPR assay. The results are shown in the following Table 2, while the NK-1 fitting dose-response curves for Compound I and IV are shown in FIGS. 2A and 2B, respectively.

1. NK-1, NK-2 and NK-3 Calcium Flux FLIPR assays:

Materials: Cell Lines: NK-1/HEK293, NK-2/HEK293, NK-3/HEK293. Media: DMEM, Invitrogen (Cat #11960), FBS, Corning (Cat #35-076-CV), G418, Invitrogen (Cat #10131-027), and Blasticidin, Invitrogen (Cat #A11139). Reagent: Fluo-4 Direct, (Invitrogen, Cat #F10471).

Experimental procedure for NK-1, NK-2 and NK-3 calcium flux FLIPR assay: Perform the assay in the following steps: 1) Cell preparation: thaw each cell (NK-1, NK-2 and NK-3) in 37° C. water bath with gentle shaking, transfer cell suspensions to 50 mL conical tubes and add plating media to 45 mL mark. Count cells using a ViCell for concentration. Re-suspend the cells in the growth media to a concentration of $10 \times 10^5$ per mL. Add 20 µL per well of the cell suspension to the 384-well plates (20,000 cells/well). Place the cells at 37° C. 5% $CO_2$ incubator overnight. 2) Calcium Flux FLIPR assay: a) Prepare Probenecid reagent by adding 1 mL FLIPR Assay Buffer to 77 mg probenecid to make 250 mM solution. b) Prepare assay reagent (2×8 µM Fluo-4 Direct™ Loading Buffer): Thaw one vial of Fluo-4 Direct™ crystals, add 10 mL of FLIPR Assay Buffer to the Vial; add 0.2 mL of Probenecid to each 10 mL vial of Fluo-Direct. c) Compounds preparation: The compounds are serially diluted in 100% DMSO 1:3 for 10 pts by Echo. Then dispense 900 nL of compounds to the 384-compound plate. Remove cell plate from incubator and gently dispense 20 µL of 2×Fluo-4 Direct™ to 384 well cell culture plate. Incubate for 50 min at 37° C. 5% $CO_2$ and 10 min at room temperature. Remove cell plate from incubator and place it into FLIPR (Molecular Devices). Place compound plate and tip box into FLIPR. For the dose response curve (DRC) plate: a) Run the Protocol on FLIPRTETRA. b) Transfer 10 µL of assay buffer from 384-well plate to the cell plates. c) Read fluorescence signal. d) Transfer 10 µL of the compounds from the DRC plate to the cell plates. e) Read fluorescence signal. f) Calculate the "Max-Min" starting from Read 90 to Maximum allowed. Calculate the $EC_{80}$ values for each cell line using FLIPR. g) Prepare 6×$EC_{80}$ concentrations of agonist reference compounds. For the compound plate in antagonist test: a) Run the Protocol on FLIPRTETRA. b) Transfer 10 µL of references and compounds from the compound plate to the cell plates. c) Read fluorescence signal. d) Transfer 10 μL of 6×EC$_{80}$ concentrations of agonist reference compounds to the cell plates. e) Read fluorescence signal. f) For antagonist test, calculate the "Max-Min" starting from Read 90 to Maximum allowed. h) Analyze the data using GraphPad Prism 5.0.

2. Experimental results.

TABLE 2

Data Summary of Compound Antagonist Activity on NK-1/2/3 Receptor by Calcium Flux FLIPR Assay.

| NKs FLIPR Test Mode | Compound | IC$_{50}$ (nM) | Max dose (nM) | % Inhibition @Max dose |
|---|---|---|---|---|
| NK-1 | Compound I | 6.15 | 10000 | 102 |
|  | Compound IV | 22.2 | 10000 | 101 |
| NK-2 | Compound I | >10000 | 10000 | 15 |
|  | Compound IV | >10000 | 10000 | 1 |
| NK-3 | Compound I | >10000 | 10000 | 26 |
|  | Compound IV | >10000 | 10000 | 29 |

C. Pharmacokinetic Studies.

For rat pharmacokinetic studies, male Sprague-Dawley rats were housed individually and fasted overnight before use. For Compound I and reference compound CP-122721, a single dose was administered to each rat in two groups (n=5/group) via intravenous (i.v.) administration at 4 mg/kg and oral (p.o.) administration of 20 mg/kg, respectively.

Reference compound CP-122721 is (2S,3S)-N-[[2-methoxy-5-(trifluoromethoxy)phenyl]methyl]-2-phenylpiperidin-3-amine and has the structure:

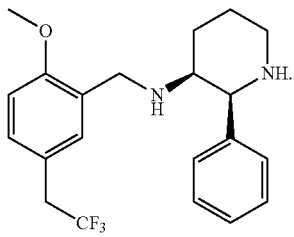

Figure 3A:
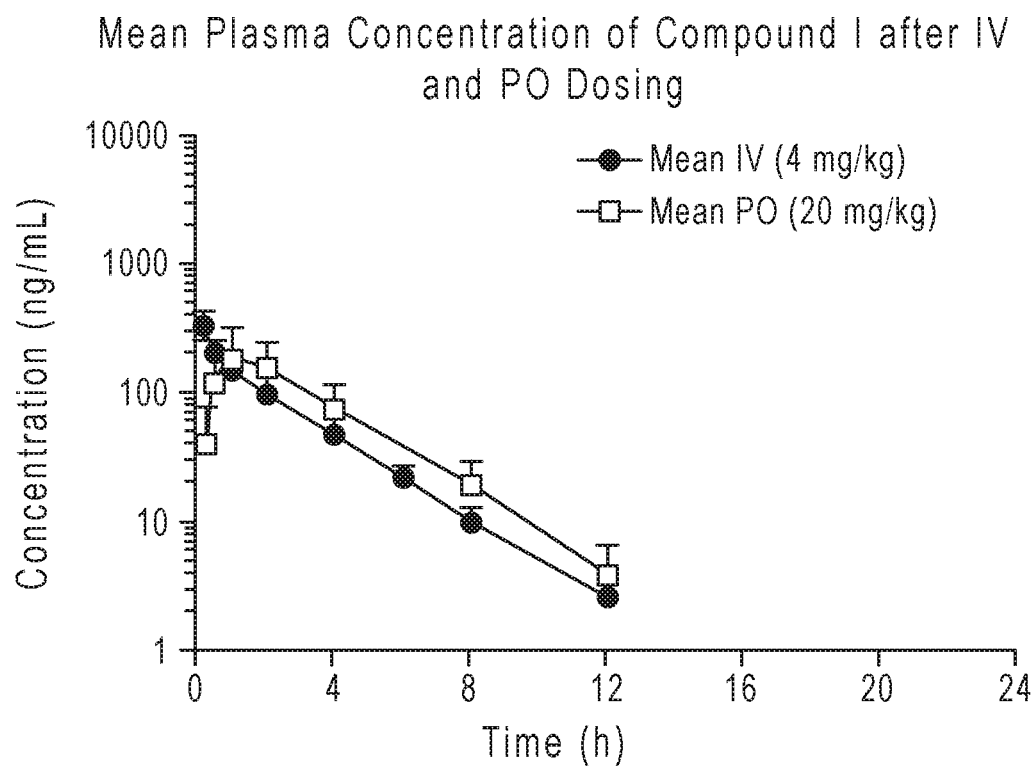
FIGS. 3A and 4B show pharmacokinetic parameters of Compound I and CP-122721 in rats.
Figure 3B:
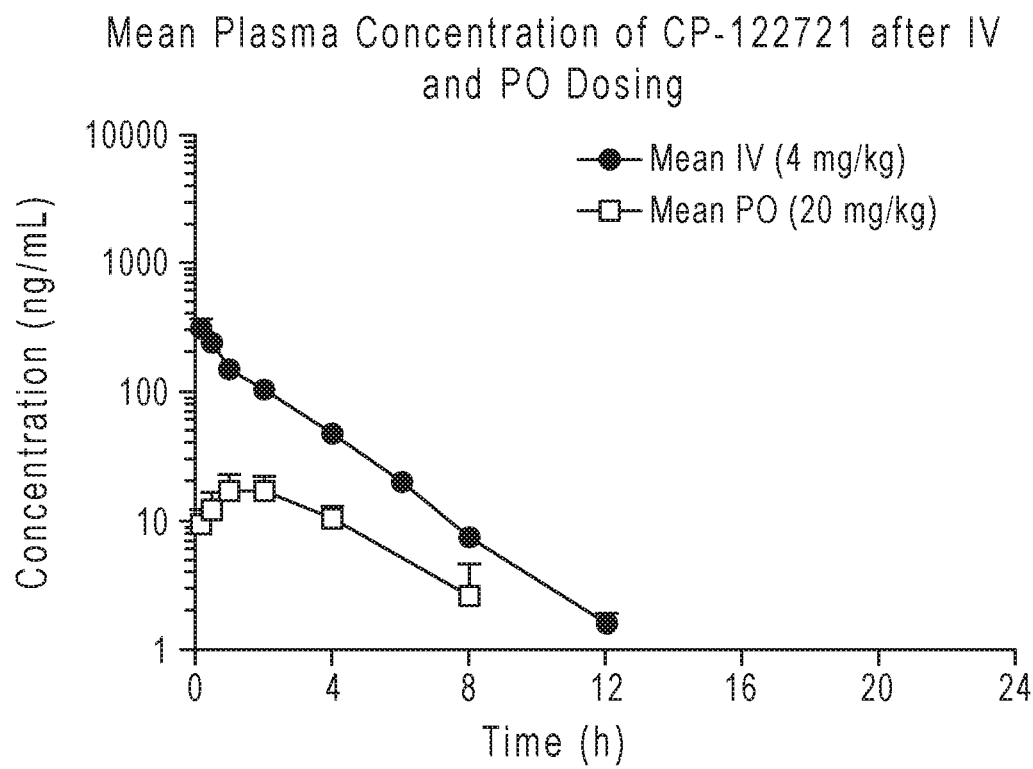

The vehicle used for i.v. administration was 10% HP-β-CD. The vehicle used for p.o. administration was 0.5% CMC-Na/0.1% Tween 80 in saline. Blood samples were collected at specified time-points following administration to individual rats within i.v. (pre-dose, 10 min, 0.5 h, 1 h, 2 h, 4 h, 6 h, 8 h, 12 h) and p.o. (pre-dose, 15 min, 0.5 h, 1 h, 2 h, 4 h, 8 h, 12 h, 24 h) group. Blood samples were clotted on ice immediately, plasma samples were then isolated by centrifugation and stored frozen (−80° C.) until further analysis. The concentrations of Compound I and CP-122721 were individually determined by LC/MS/MS assay. Various pharmacokinetic parameters were calculated using Phoenix™ WinNonlin® software. To quantify the bioconversion efficiency of the Compound I and CP-122721 in the circulation system, the bioavailability of Compound I and CP-122721 after p.o. administration was calculated. The results are showed in Table 3, FIGS. 3A and 3B.

TABLE 3

Rat pharmacokinetic parameters of Compound I and CP-122721.

|  |  | AUC$_{0-last}$ (ng*h/mL) | T$_{1/2}$ (h) | T$_{max}$ (h) | C$_{max}$ (ng/mL) | Bioavailability (%) |
|---|---|---|---|---|---|---|
| Compound I at 4 mg/kg | i.v. | 663 | 1.84 |  |  |  |
| Compound I at 20 mg/kg | p.o. | 740 | 1.90 | 1.40 | 202 | 22.4 |
| CP-122721 at 4 mg/kg | i.v. | 613 | 1.66 |  |  |  |
| CP-122721 at 20 mg/kg | p.o. | 78.7 | 1.92 | 1.40 | 17.8 | 2.6 |

D. Compound I testing on cisplatin-induced emesis in ferrets.

1. Objectives

To investigate the anti-emetic potential of Compound I by preventing cisplatin-induced acute and delayed emesis in the ferret. Aprepitant was used as a positive control in this study.

2. Methods

1) Animals.

40 castrated male ferrets weighing between 1.2 and 2.3 kg were used, which were obtained from Wuxi Sangosho Biotechnology Co. Ltd. (Wuxi, Jiangsu, China) and housed in groups of 2-3 at 24±1° C. with at 50±5% humidity. Artificial lighting was provided between 06:00 to 18:00 h. Water and dry pelleted cat chow were given ad libitum, unless otherwise stated. All experiments were conducted under license from the Government of the Hong Kong SAR and the Animal Experimentation Ethics Committee, The Chinese University of Hong Kong.

2) Drug used.

Compound I and aprepitant were supplied by XW Laboratories, Inc, China and were dissolved in distilled water. Cisplatin (Lot #MKBR1947V) was from Sigma-Aldrich, St. Louis, USA, and was dissolved in 0.9% w/v saline adjusted to pH 4 with 0.1N HCl. Doses were expressed as the free base, unless otherwise stated.

3) Cisplatin-induced acute and delayed emesis experiments in the ferret

On the day of the experiment, groups of ferrets were administered Compound I (0.1, 0.3, 1 mg/kg, p.o.), aprepitant (1 mg/kg, p.o.), or distilled water (vehicle control, 1 mL/kg, p.o.) 2 h before cisplatin (5 mg/kg, i.p.) and then the treatments were continued at 24 h intervals (at 24 and 48 h post cisplatin). Emesis was characterized by rhythmic abdominal contractions that were either associated with the forceful oral expulsion of solid or liquid material from the gastrointestinal tract (i.e., vomiting), or not associated with the passage of material (i.e., retching movements). Consecutive episodes of retching and/or vomiting were considered separate when the animal changed its location in the observation cage, or when the interval between episodes exceeded 5 seconds.

4) Data analysis.

GraphPad Prism 8 (GraphPad Software, La Jolla, Calif., United States) was used to perform statistical comparisons. Animal emesis behaviours like retching and vomiting were analyzed using a one-way analysis of variance followed by Tukey's multiple comparisons tests. The results are expressed as the mean±SEM. In all cases, differences between treatment groups were considered significant when the p value was less than 0.05.

3. Results

1) The effect of orally administered Compound I in comparison with aprepitant on the total numbers of episodes, retches and vomits induced by cisplatin in a 72 h observation time.

Figure 4A:
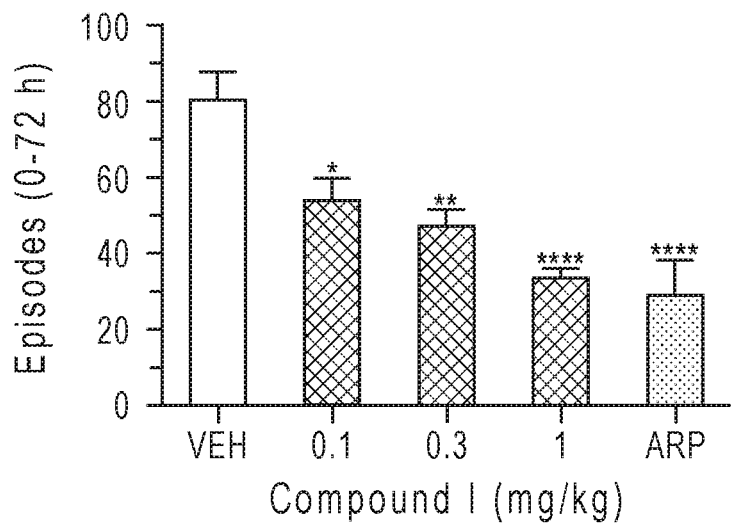
Figure 4B:
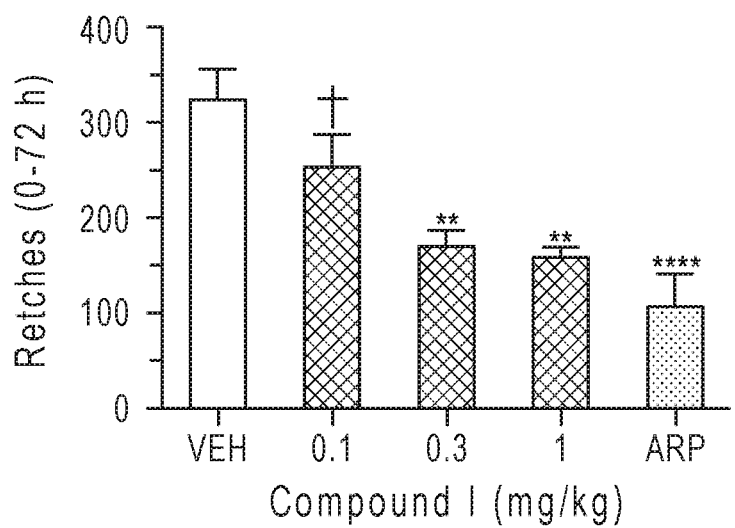
Figure 4C:
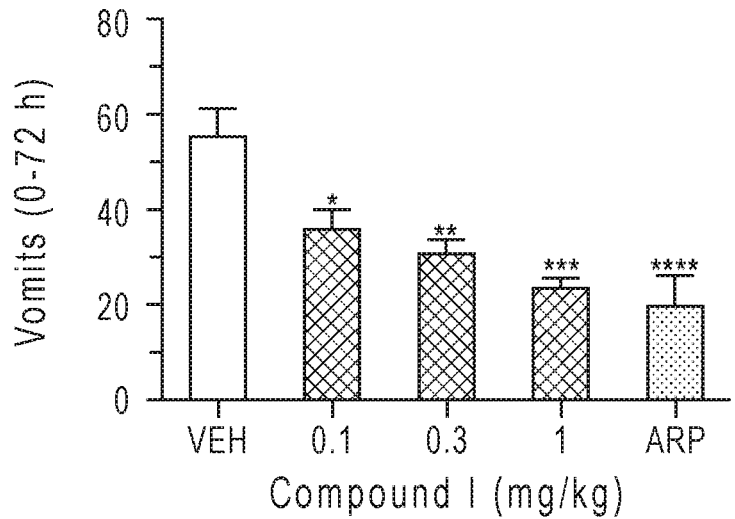
Figure 5A:
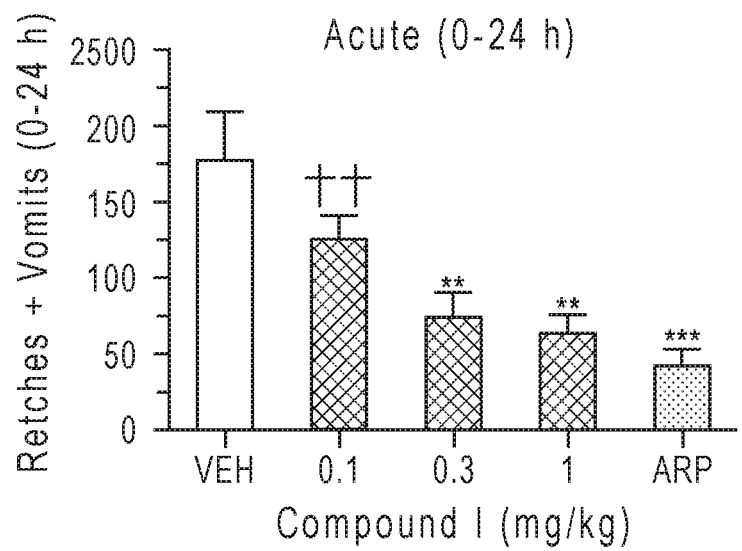
FIGS. 5A-5E show the effect of Compound I and aprepitant on the retching and/or vomiting induced by cisplatin during the acute and delayed phases.
Figure 5B:
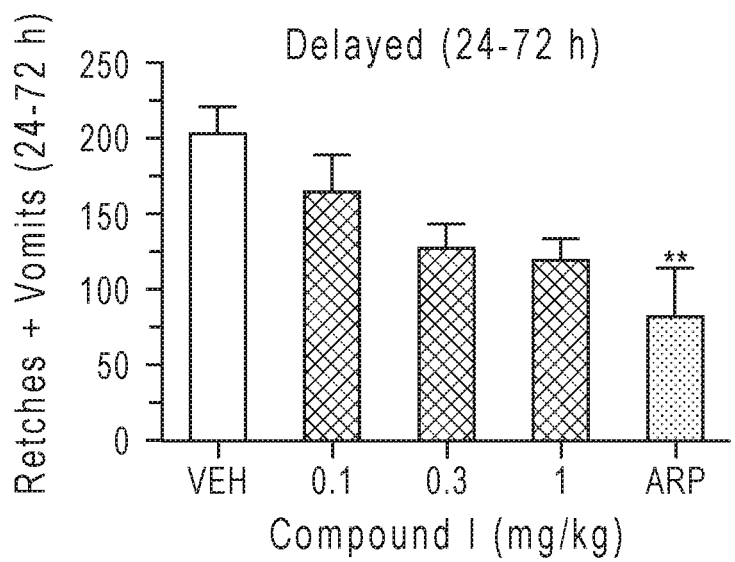
Figure 5C:
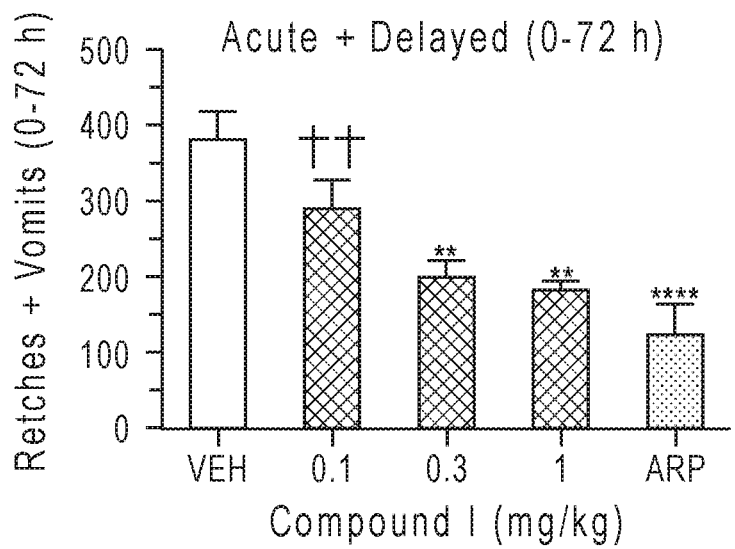
Figure 5D:
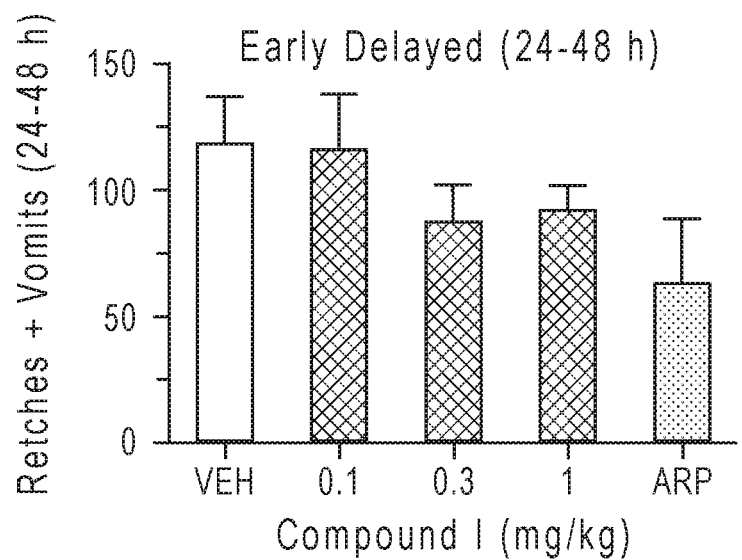
Figure 5E:
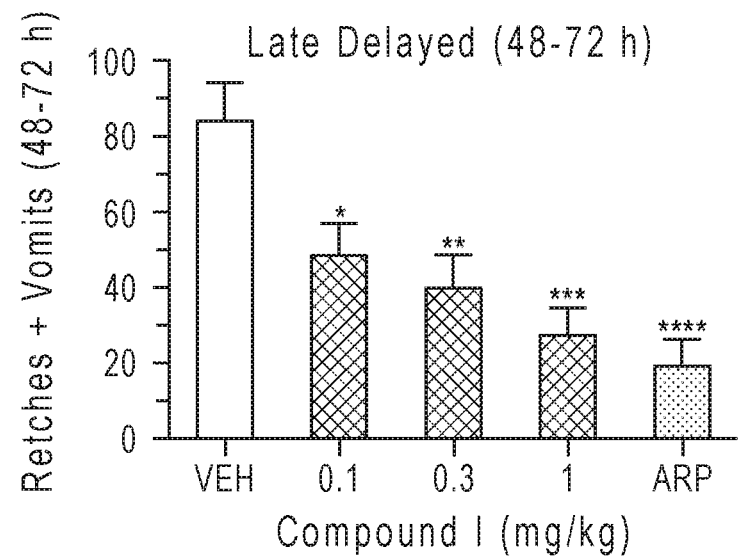

Compound I dose-dependently reduced the total numbers of episodes, retches and vomits during the entire 72 h observation period; maximum reductions at 1 mg/kg were 59.0 ($P<0.05$), 51.3 ($P<0.01$) and 57.3% ($P<0.001$), respectively (FIGS. 4A-4C). Comparatively, aprepitant at 1 mg/kg reduced the total numbers of episodes, retches and vomits during the entire 72 h observation period by 64.0 ($P<0.0001$), 67.9 ($P<0.0001$) and 64.6 ($P<0.0001$)%, respectively; it was superior (46% superior) to the 21.9% reduction of retches seen with the lowest dose of Compound I, 0.1 mg/kg ($P<0.05$). However, aprepitant was not superior to the higher doses of Compound I (0.3 and 1 mg/kg; FIGS. 4A-4C).

2) The effect of orally administered Compound I in comparison with aprepitant on the retching and/or vomiting induced by cisplatin during the acute and delayed phases.

Compound I dose-dependently reduced the retching+vomiting response on days 1 (acute), 2, and 3 (see FIGS. 5A-5E). The maximal reductions at 1 mg/kg were 64.5 ($P<0.01$), 22.7 (non-significant, $P>0.05$), and 67.5 ($P<0.001$) %, respectively. Comparatively, aprepitant at 1 mg/kg reduced the retching+vomiting response on day 1 (acute), 2 and 3 by 76.5 ($P<0.01$), 46.7 (non-significant, $P>0.05$) and 73.3 ($P<0.001$)%, respectively.

Compound I did not provide an antagonism of the retching+vomiting seen during the entire delayed (24-72 h) phase; the maximum non-significant reduction at 1 mg/kg was 41.3% ($P>0.05$). However, aprepitant reduced the entire delayed (24-72 h) phase significantly by 59.4% ($P<0.01$). Aprepitant was not superior to Compound I to reduce the delayed phase ($P>0.05$). The overall combined acute and delayed response (0-72 h) was antagonized dose-dependently by Compound I; a maximum 52.2% reduction was seen at 1 mg/kg ($P<0.01$). Comparatively, aprepitant at 1 mg/kg reduced the total numbers of retches+vomits during the entire 72 h observation period by 67.4 ($P<0.0001$); it was 43.5% superior to the 23.9% reduction of retches seen with the lowest dose of Compound I, 0.1 mg/kg ($P<0.01$). However, aprepitant was not superior to the higher doses of Compound I (0.3 and 1 mg/kg, $P>0.05$).

4. Conclusions

Both Compound I and aprepitant had antiemetic effects. Aprepitant 1 mg/kg appeared superior to the lowest dose of Compound I, 0.1 mg/kg, but it was not superior to the higher doses of Compound I at 0.3 or 1 mg/kg. Overall, as a potent NK-1 receptor antagonist, Compound I 1 mg/kg had comparable antiemetic with aprepitant.

Finally, it should be noted that there are other ways to practice the invention. Accordingly, embodiments of the present invention are to be described as examples, but the present invention is not limited to the contents described, further modifications may be made within the scope of the present invention or the equivalents added in the claims.

All publications or patents cited herein are incorporated by reference in this invention.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having the structure of Formula (B):

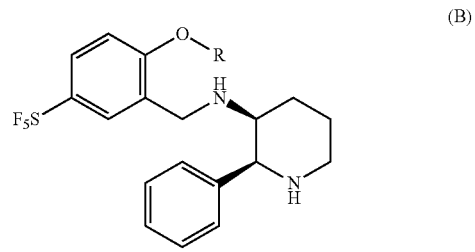

(B)

or a pharmaceutically acceptable salt thereof, wherein R is selected from $C_1$-$C_6$ alkyl.

2. The compound according to claim 1, wherein R is selected from methyl, ethyl, and isopropyl.

3. The compound of claim 1, wherein the compound is (2S,3S)-N-(2-methoxy-5-(pentafluorosulfanyl)benzyl)-2-phenylpiperidin-3-amine (I) or a pharmaceutically acceptable salt thereof:

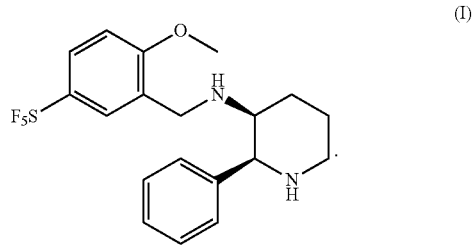

(I)

4. The compound of claim 1, wherein the compound is (2S,3S)-N-(2-ethoxy-5-(pentafluorosulfanyl)benzyl)-2-phenylpiperidin-3-amine or a pharmaceutically acceptable salt thereof:

(II)

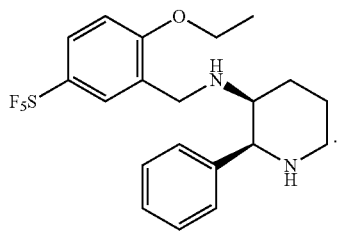

5. The compound of claim 1, wherein the compound is (2S,3S)-N-(2-isopropoxy-5-(pentafluorosulfanyl)benzyl)-2-phenylpiperidin-3-amine (III) or a pharmaceutically acceptable salt thereof:

(III)

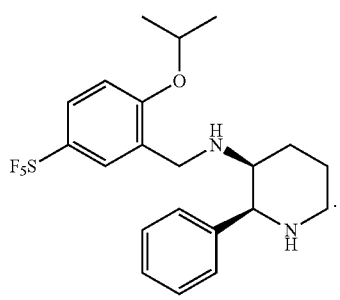

6. The compound of claim 1, wherein the compound is (2S,3S)-N-(2-(methoxy-d₃)-5-(pentafluorosulfanyl)benzyl)-2-phenylpiperidin-3-amine (IV) or a pharmaceutically acceptable salt thereof:

(IV)

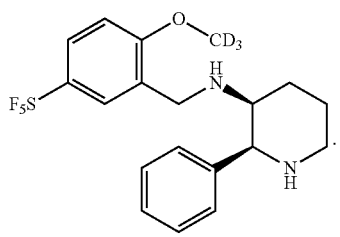

7. A compound (2S,3S)-N-(2-methoxy-4-(pentafluorosulfanyl)benzyl)-2-phenylpiperidin-3-amine (V) or a pharmaceutically acceptable salt thereof:

(V)

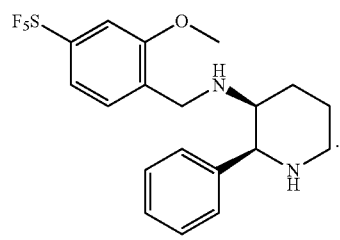

8. A pharmaceutical composition comprising the compound of claim 1 or a pharmaceutically acceptable salt thereof.

9. The pharmaceutical composition of claim 8, wherein the pharmaceutical composition further comprises a serotonin 5-HT₃ antagonist, a glucocorticoid, or a combination thereof.

10. The pharmaceutical composition of claim 8, wherein the pharmaceutical composition is an oral formulation.

11. The pharmaceutical composition of claim 8, wherein the pharmaceutical composition is an oral dosage form.

12. The pharmaceutical composition of claim 8, wherein the pharmaceutical composition is an intravenous formulation.

13. A pharmaceutical composition comprising the compound of claim 3 or a pharmaceutically acceptable salt thereof.

14. The pharmaceutical composition of claim 13, wherein the pharmaceutical composition further comprises a serotonin 5-HT₃ antagonist, a glucocorticoid, or a combination thereof.

15. The pharmaceutical composition of claim 13, wherein the pharmaceutical composition is an oral formulation.

16. The pharmaceutical composition of claim 13, wherein the pharmaceutical composition is an oral dosage form.

17. The pharmaceutical composition of claim 13, wherein the pharmaceutical composition is an intravenous formulation.

* * * * *